United States Patent
Muro-Galindo et al.

(10) Patent No.: US 9,901,625 B2
(45) Date of Patent: Feb. 27, 2018

(54) METHODS OF REGULATING UPTAKE AND TRANSCELLULAR TRANSPORT OF LEUKOCYTES AND THERAPEUTICS

(71) Applicant: University of Maryland, College Park, College Park, MD (US)

(72) Inventors: Silvia Muro-Galindo, Silver Spring, MD (US); Daniel Serrano, Hyattsville, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 0 days.

(21) Appl. No.: 13/652,165

(22) Filed: Oct. 15, 2012

(65) Prior Publication Data

US 2013/0095091 A1 Apr. 18, 2013

Related U.S. Application Data

(60) Provisional application No. 61/547,687, filed on Oct. 15, 2011.

(51) Int. Cl.
*A61K 38/46* (2006.01)
*A61K 31/231* (2006.01)
(Continued)

(52) U.S. Cl.
CPC .......... *A61K 38/465* (2013.01); *A61K 31/164* (2013.01); *A61K 31/231* (2013.01);
(Continued)

(58) Field of Classification Search
CPC .......... A61K 47/48238; A61K 51/0491; A61K 47/48092; A61K 2039/6031;
(Continued)

(56) References Cited

U.S. PATENT DOCUMENTS

| 5,919,754 A | 7/1999 | Altieri et al. |
| 6,676,940 B2 | 1/2004 | Altieri et al. |

(Continued)

FOREIGN PATENT DOCUMENTS

| DE | 69331193 T2 | 4/2002 |
| EP | 2377542 A2 | 10/2011 |

(Continued)

OTHER PUBLICATIONS

Sauvage et al., Eur. J. Biochem. 267: 955-962 (2000).*

(Continued)

*Primary Examiner* — Erin M. Bowers
(74) *Attorney, Agent, or Firm* — Hultquist, PLLC; Steven J. Hultquist

(57) ABSTRACT

Methods for controlling and regulating engulfment, uptake and/or transcellular transport at a stage following initial engagement of an agent to the endothelium are provided, based on the identification of CAM-mediated endocytosis and the sphingomyelin/ceramide pathway as active steps in transcellular TEM. Administration of regulators relating to the identified pathways, such as NHE1, sphingomyelinases, acid sphingomyelinase and ceramide, permit control and regulation of uptake and transcellular transport. Control and regulation of uptake and/or transcellular transport is applicable in strategies to modulate inflammation, provide controlled and/or targeted delivery of agents, control pathogenic invasion, recover action of an inhibited CAM-mediated uptake or transendothelial pathway, or provide uptake or transendothelial transport by targeting cell surface markers other than ICAM-1.

14 Claims, 16 Drawing Sheets
(5 of 16 Drawing Sheet(s) Filed in Color)

(51) Int. Cl.
| | |
|---|---|
| A61K 38/16 | (2006.01) |
| A61K 31/164 | (2006.01) |
| A61K 31/4965 | (2006.01) |
| A61K 31/55 | (2006.01) |
| A61K 31/688 | (2006.01) |

(52) U.S. Cl.
CPC .......... *A61K 31/4965* (2013.01); *A61K 31/55* (2013.01); *A61K 31/688* (2013.01); *A61K 38/16* (2013.01)

(58) Field of Classification Search
CPC .................. C07K 16/2821; C12N 9/2408; C12N 9/2465; C12Y 302/0102; C12Y 302/01022
See application file for complete search history.

(56) References Cited

U.S. PATENT DOCUMENTS

| 6,737,058 | B2 | 5/2004 | Altieri et al. |
|---|---|---|---|
| 7,223,395 | B2 | 5/2007 | Muller et al. |
| 8,088,382 | B2 | 1/2012 | Muller et al. |
| 2002/0131970 | A1 | 9/2002 | Altieri et al. |
| 2002/0169280 | A1 | 11/2002 | Altieri et al. |
| 2004/0029779 | A1* | 2/2004 | Zhu .................. A61K 31/557 424/94.1 |
| 2010/0168219 | A1 | 7/2010 | Alexander |
| 2011/0177155 | A1 | 7/2011 | Peer et al. |
| 2012/0082732 | A1 | 4/2012 | Fehre et al. |

FOREIGN PATENT DOCUMENTS

| WO | 9325218 A1 | 12/1993 |
|---|---|---|
| WO | 9415641 A1 | 7/1994 |
| WO | 9528946 A1 | 11/1995 |
| WO | 2011011500 A1 | 1/2011 |
| WO | 2011044329 A2 | 4/2011 |
| WO | 2011112732 A2 | 9/2011 |
| WO | 2011134060 A1 | 11/2011 |
| WO | 2012046001 A1 | 4/2012 |

OTHER PUBLICATIONS

Muro et al., Am. J. Physiol. Lung Cell Mol. Physiol. 290: L809-L817 (2006).*
Bonfils et al., Nucleic Acids Res. 20(17): 4621-4629 (1992).*
Hu et al., J. Biol. Chem. 265(23): 13864-13870 (1990).*
Braulke et al., Eur. J. Biochem. 189: 609-616 (1990).*
Goncalves et al., Mol. Ther. 10(2): 373-385 (2004).*
Seres et al., J. Immunol. 165: 3333-3340 (2000).*
Dhami et al., J. Biol. Chem. 279(2): 1526-1532 (2004).*
Miranda et al., FASEB J. 14: 1988-1995 (2000).*
Chatterjee, J. Biol. Chem. 268(5): 3401-3406 (1993).*
Teichgraeber, V., et al., "Ceramide accumulation mediates inflammation, cell death and infection susceptibility in cystic fibrosis", "Nature Medicine", Apr. 2008, pp. 382-391, vol. 14, No. 4.
Tilghman, R., et al., "E-selectin and ICAM-1 are incorporated into detergent-insoluble membrane domains following clustering in endothelial cells", "FEBS Letters", Jul. 16, 2002, pp. 83-87, vol. 525.
Utermoehlen, O., et al., "Fusogenicity of membranes: The impact of acid sphingomyelinase on innate immune responses", "Immunobiology", 2008, pp. 307-314, vol. 213.
Van Buul, J., et al., "RhoG regulates endothelial apical cup assembly downstream from ICAM1 engagement and is involved in leukocyte trans-endothelial migration", "The Journal of Cell Biology", Sep. 17, 2007, pp. 1279-1293, vol. 178, No. 7.
Van Buul, J., et al., "Inside-Out Regulation of ICAM-1 Dynamics in TNF-alpha-Activated Endothelium", "PLoS One", Jun. 28, 2010, pp. 1-14, vol. 5, No. 6, e11336.
Villanueva, F., et al., "Microbubbles Targeted to Intercellular Adhesion Molecule-1 Bind to Activated Coronary Artery Endothelial Cells", "Circulation", 1998, pp. 1-5, vol. 98.
Von Bismarck, P., et al., "Improved Pulmonary Function by Acid Sphingomyelinase Inhibition in a Newborn Piglet Lavage Model", "Am J Respir Crit Care Med", Feb. 28, 2008, pp. 1233-1241, vol. 177.
Weller, G., et al., "Modulating Targeted Adhesion of an Ultrasound Contrast Agent to Dysfunctional Endothelium", "Annals of Biomedical Engineering", 2002, pp. 1012-1019, vol. 30.
Willingham, M., et al., "Morphologic study of the internalization of a lysosomal enzyme by the mannose 6-phosphate receptor in cultured Chinese hamster ovary cells", "Proc. Natl Acad. Sci. USA", Nov. 1981, pp. 6967-6971, vol. 78, No. 11.
Yang, L., et al., "Endothelial Cell Cortactin Phosphorylation by Src Contributes to Polymorphonuclear Leukocyte Transmigration In Vitro", "Circulation Research", Dec. 29, 2005, pp. 394-402, S1-S3, vol. 98.
Yang, L, et al., "ICAM-1 regulates neutrophil adhesion and transcellular migration of TNF-alpha-activated vascular endothelium under flow", "Blood", Jul. 15, 2005, pp. 584-592, vol. 106.
Zeidan, Y., et al., "Remodeling of cellular cytoskeleton by the acid sphingomyelinase/ceramide pathway", "The Journal of Cell Biology", Apr. 21, 2008, pp. 335-350, vol. 181, No. 2.
Zha, X., et al., "Sphingomyelinase Treatment Induces ATP-independent Endocytosis", "The Journal of Cell Biology", Jan. 12, 1998, pp. 39-47, vol. 140, No. 1.
Allingham, M., et al., "ICAM-1-Mediated, Src- and Pyk2-Dependent Vascular Endothelial Cadherin Tyrosine Phosphorylation is Required for Leukocyte Transendothelial Migration", "The Journal of Immunology", 2007, pp. 4053-1064, vol. 179.
Altura, B., et al., "Sphingomyelinase and ceramide analogs induce vasoconstriction and leukocyte-endothelial interactions in cerebral venules in the intact rat brain: Insight into mechanisms and possible relation to brain injury and stroke", "Brain Research Bulletin", 2002, pp. 271-278, vol. 58, No. 3.
Andrews, N., "Regulated secretion of conventional lysosomes", "Trends in Cell Biology", Aug. 2000, pp. 316-321, vol. 10.
Barreiro, O., et al., "Dynamic interaction of VCAM-1 and ICAM-1 with moesin and ezrin in a novel endothelial docking structure for adherent leukocytes", "The Journal of Cell Biology", Jun. 24, 2002, pp. 1233-1245, vol. 157, No. 7.
Barreiro, O., et al., "Endothelial tetraspanin microdomains regulate leukocyte firm adhesion during extravasation", "Blood", Dec. 9, 2004, pp. 2852-2861, vol. 105.
Bourguignon, L., et al., "CD44 Interaction with Na+-H+ Exchanger (NHE1) Creates Acidic Microenvironments Leading to Hyaluronidase-2 and Cathepsin B Activation and Breast Tumor Cell Invasion", "The Journal of Biological Chemistry", Jun. 25, 2004, pp. 26991-27007, vol. 279, No. 26.
Carman, C., et al., "A transmigratory cup in leukocyte diapedesis both through individual vascular endothelial cells and between them", "The Journal of Cell Biology", Oct. 25, 2004, pp. 377-388, vol. 167, No. 2.
Carman, C. et al., "Transcellular Diapedesis is Initiated by Invasive Podosomes", "Immunity", Jun. 2007, pp. 784-797, vol. 26.
Danilov, S., et al., "Lung uptake of antibodies to endothelial antigens: key determinants of vascular immunotargeting", "Am J Physiol Lung Cell Mol Physiol", 2001, pp. L1335-L1347, vol. 280.
Dejana, E., "Endothelial Cell-Cell Junctions: Happy Together", "Nature Reviews: Molecular Cell Biology", Apr. 2004, pp. 261-270, vol. 5.
Denker, S., et al., "Direct Binding of the Na-H Exchanger NHE1 to ERM Proteins Regulates the Cortical Cytoskeleton and Cell Shape Independently of H+ Translocation", "Molecular Cell", Dec. 2000, pp. 1425-1436, vol. 6.
Dong, Q., et al., "A General Strategy for Isolation of Endothelial Cells From Murine Tissues", "Arteriosclerosis, Thrombosis, and Vascular Biology", 1997, pp. 1599-1604, vol. 17.
Dvorak, A., et al., "The Vesiculo-Vacuolar Organelle (VVO): A New Endothelial Cell Permeability Organelle", "The Journal of Histochemistry & Cytochemistry", Apr. 1, 2001, pp. 419-431, vol. 49, No. 4.

(56) References Cited

OTHER PUBLICATIONS

Garnacho, C., et al., "Delivery of Acid Sphingomyelinase in Normal and Niemann-Pick Disease Mice Using Intercellular Adhesion Molecule-1-Targeted Polymer Nanocarriers", "Journal of Pharmacology and Experimental Therapeutics", May 2008, pp. 400-408, vol. 325, No. 2.

Garnacho, C., et al., "RhoA activation and actin reorganization involved in endothelial CAM-mediated endocytosis of anti-PECAM carriers: critical role for tyrosine 686 in the cytoplasmic tail of PECAM-1", "Blood", Jan. 8, 2008, pp. 3024-3033, vol. 111.

Gerard, A. et al., "The Rac activator Tiam1 controls efficient T-cell trafficking and route of transendothelial migration", "Blood", Jan. 12, 2009, pp. 6138-6147, vol. 113.

Hallahan, D., et al., "Intercellular adhesion molecule 1 knockout abrogates radiation induced pulmonary inflammation", "Proc. Natl. Acad. Sci.", Jun. 1997, pp. 6432-6437, vol. 94.

Hillebrand, U., et al., "17beta-estradiol increases volume, apical surface and elasticity of human endothelium mediated by Na+/H+ exchange", "Cardiovascular Research", Jan. 17, 2006, pp. 916-924, vol. 69.

Holopainen, J., et al., "Sphingomyelinase Induces Lipid Microdomain Formation in a Fluid Phosphatidylcholine/Sphingomyelin Membrane", "Biochemistry", 1998, pp. 17562-17570, vol. 37.

Holopainen, J., et al., "Vectorial Budding of Vesicles by Asymmetrical Enzymatic Formation of Ceramide in Giant Liposomes", "Biophysical Journal", Feb. 2000, pp. 830-838, vol. 78.

Hopkins, A., et al., "ICAM-1: targeted docking for exogenous as well as endogenous ligands", "Advanced Drug Delivery Reviews", 2004, pp. 763-778, vol. 56.

Horinouchi, K., et al., "Acid sphingomyelinase deficient mice: a model of types A and B Niemann-Pick disease", "Nature Genetics", Jul. 1995, pp. 288-293, vol. 10.

Huang, A., et al., "Endothelial Cell Cytosolic Free Calcium Regulates Neutrophil Migration across Monolayers of Endothelial Cells", "The Journal of Cell Biology", Mar. 1993, pp. 1371-1380, vol. 120, No. 6.

Hubbard, A., et al., "Intercellular Adhesion Molecule-1 (ICAM-1) Expression and Cell Signaling Cascades", "Free Radical Biology & Medicine", 2000, pp. 1379-1386, vol. 28, No. 9.

Jenkins, R., et al., "Roles and regulation of secretory and lysosomal acid sphingomyelinase", "Cellular Signalling", Jan. 19, 2009, pp. 836-846, vol. 21.

Kavanaugh, A., et al., "Repeat Treatment of Rheumatoid Arthiritis Patients with a Murine Anti-intercellular Adhesion Molcule 1 Monoclonal Antibody", "Arthritis & Rheumatism", May 1997, pp. 849-853, vol. 40, No. 5.

Kleyman, T., et al., "Amiloride and Its Analogs as Tools in the Study of Ion Transport", "J. Membrane Biol.", 1988, pp. 1-21, vol. 105.

Ley, K., et al., "Getting to the site of inflammation: the leukocyte adhesion cascade updated", "Nature Reviews: Immunology", Sep. 2007, pp. 678-689, vol. 7.

Marmon, S., et al., "Caveolin-1 Expression Determines the Route of Neutrophil Extravasation through Skin Microvasculature", "The American Journal of Pathology", Feb. 2009, pp. 684-692, vol. 174, No. 2.

Millan, J., et al., "Lymphocyte transcellular migration occurs through recruitment of endothelial ICAM-1 to caveola- and F-actin-rich domains", "Nature Cell Biology", Feb. 2006, pp. 113-123, S1-S4, vol. 8, No. 2.

Murciano, J., et al., "ICAM-directed vascular immunotargeting of antithrombotic agents to the endothelial luminal surface : Presented in part as posters at the American Thoracic Society (ATS) Meeting, May 5-10, 2000, Toronto ON, Canada", "Blood", May 15, 2003, pp. 3977-3984, vol. 101.

Muro, S., et al., "A novel endocytic pathway induced by clustering endothelial ICAM-1 or PECAM-1", "Journal of Cell Science", 2003, pp. 1599-1609, vol. 116.

Muro, S., "Chapter 117 Intercellular Adhesion Molecule-1 and Vascular Cell Adhesion Molecule-1", "The Endothelium: A Comprehensive Reference (W. Aird, Ed.)", Jan. 19, 2007, pp. 1058-1070, Publisher: Cambridge University Press, Published in: New York.

Muro, S, et al., "Control of Endothelial Targeting and Intracellular Delivery of Therapeutic Enzymes by Modulating the Size and Shape of ICAM-1-targeted Carriers", "Mol Ther.", Aug. 2008, pp. 1450-1458, vol. 16, No. 8.

Muro, S., et al., "ICAM-1 recycling in endothelial cells: a novel pathway for sustained intracellular delivery and prolonged effects of drugs", "Blood", Sep. 14, 2004, pp. 650-658, vol. 105, No. 2.

Muro, S., et al., "Control of intracellular trafficking of ICAM-1-targeted nanocarriers by endothelial Na+/H+ exchanger proteins", "Am J Physiol Lung Cell Mol Physiol", Nov. 18, 2005, pp. L809-L817, vol. 290.

Nourshargh, S., et al., "Breaching multiple barriers: leukocyte motility through venular walls and the interstitium", "Nature Reviews: Molecular Cell Biology", May 2010, pp. 366-378, vol. 11.

Oh, H., et al., "RKIKK Motif in the Intracellular Domain is Critical for Spatial and Dynamic Organization of ICAM-1: Functional Implication for the Leukocyte Adhesion and Transmigration", "Molecular Biology of the Cell", Jun. 2007, pp. 2322-2335, vol. 18.

Oh, P., et al., "Live dynamic imaging of caveolae pumping targeted antibody rapidly and specifically across endothelium in the lung", "Nature Biotechnology", Mar. 2007, pp. 327-337, vol. 25, No. 3.

Phillipson, M., et al., "Intraluminal crawling of neutrophils to emigration sites: a molecularly distinct process from adhesion in the recruitment cascade", "The Journal of Experimental Medicine", Nov. 20, 2006, pp. 2569-2575, vol. 203, No. 12.

Rebillard, A., et al., "Cisplatin-Induced Apoptosis Involves Membrane Fluidification via Inhibition of NHE1 in Human Colon Cancer Cells", "Cancer Res", Aug. 15, 2007, pp. 7865-7874, vol. 67, No. 16.

Rossin R., et al., "In Vivo Imaging of 64Cu-Labeled Polymer Nanoparticles Targeted to the Lung Endothelium", "The Journal of Nuclear Medicine", Jan. 2008, pp. 103-111, vol. 49, No. 1.

Rothlein, R., et al., "A Human Intercellular Adhesion Molecule (ICAM-1) Distinct From LFA-1", "The Journal of Immunology", Aug. 15, 1986, pp. 1270-1274, vol. 137, No. 4.

Rotolo, J., et al., "Cytolytic T cells induce ceramide-rich platforms in target cell membranes to initiate graft-versus-host disease", "Blood", Aug. 7, 2009, pp. 3693-3706, vol. 114.

Sakhalkar, H., et al., "Leukocyte-inspired biodegradable particles that selectively and avidly adhere to inflamed endothelium in vitro and in vivo", "PNAS", Dec. 23, 2003, pp. 15895-15900, vol. 100, No. 26.

Shaw, S., et al., "Reduced Expression of Junctional Adhesion Molecule and Platelet/Endothelial Cell Adhesion Molecule-1 (CD31) at Human Vascular Endothelial Junctions by Cytokines Tumor Necrosis Factor-alpha Plus Interferon-gamma Does Not Reduce Leukocyte Transmigration Under Flow", "Am J Pathol", Dec. 2001, pp. 2281-2291, vol. 159, No. 6.

Silva, L., et al., "Lipid Raft Composition Modulates Sphingomyelinase Activity and Ceramide-Induced Membrane Physical Alterations", "Biophysical Journal", Apr. 2009, pp. 3210-3222, vol. 96.

Takei, Y., et al., "Expression of ICAM-1 is Involved in the Mechanism of Liver Injury During Liver Transplantation: Therapeutic Usefulness of the F(ab')2 Fragment of an Anti-ICAM-1 Monoclonal Antibody", "Transplantation Proceedings", Apr. 1996, pp. 1103-1105, vol. 28, No. 2.

Tam, C., et al., "Exocytosis of acid sphingomyelinase by wounded cells promotes endocytosis and plasma membrane repair", "J. Cell Biol.", Jun. 7, 2010, pp. 1027-1038, vol. 189, No. 6.

Note: For the non-patent literature citations that no month of publication is indicated, the year of publication is more than 1 year prior to the effective filing date of the present application.

* cited by examiner

METHODS OF REGULATING UPTAKE AND TRANSCELLULAR TRANSPORT OF LEUKOCYTES AND THERAPEUTICS

CROSS REFERENCE TO RELATED APPLICATIONS

This application claims the benefit of U.S. Provisional Patent Application No. 61/547,687. The disclosure of U.S. Provisional Patent Application No. 61/547,687 is hereby incorporated herein by reference in its entirety, for all purposes.

STATEMENT REGARDING FEDERALLY SPONSORED RESEARCH

This invention was made with government support under R01 HL098416-01 awarded by the National Institutes of Health. The government has certain rights in the invention.

FIELD OF THE INVENTION

The present invention relates to methods of regulating engulfment or docking structures, vesicular uptake, and transcellular migration of leukocytes and other agents and relates to methods of utilizing regulated engulfment, uptake, and transcellular endothelial migration.

DESCRIPTION OF THE RELATED ART

Leukocyte recruitment to inflammatory sites requires extravasation across the vascular endothelium (Ley K, et al. (2007) Nat Rev Immunol 7:678-689; Nourshargh S, et al. (2010) Nat Rev Mol Cell Bio 111:366-378). This occurs through the sequential steps of white blood cell (WBC) rolling over endothelial cells (ECs), firm arrest, lateral crawling, and transendothelial migration (TEM) (Ley et al.; Nourshargh et al.). The most studied route of TEM is the paracellular pathway, which involves dissociation of endothelial junctions and leukocyte extravasation between adjacent ECs (Dejana, E (2004) Nat Rev Mol Cell Bio 15:261-270; Ley et al., 2007). WBC TEM also occurs via the transcellular pathway, by crossing the EC body independently of junction opening (Dvorak, A M et al. (2001) J Histochem Cytochem 49:419-432; Carman C V, et al. (2004) J. of Cell Biol. 167:377-388; Millan J, et al. (2006) Nat Cell Biol 8:113-123), which has been observed in cell culture (Carman et al. 2004; Yang L, et al. (2005) Blood 106:584-592; Millan et al., 2006) and in vivo (Dvorak et al.; Phillipson M, et al. J Exp Med 203:2569-2575; Marmon S, et al. (2009) Am J Path 01 1 74:684-692).

The mechanisms regulating these two TEM routes are overlapping and not fully understood (Dejana et al.; Ley et al.; Nourshargh et al.). They are both mediated by multiple interactions between molecules on the surface of the leukocytes and ECs (Ley et al.; Nourshargh et al.). This is the case for intercellular adhesion molecule 1 (ICAM-1), a transmembrane glycoprotein of the immunoglobulin superfamily (Muro S (2007) Intercellular Adhesion Molecule-1 and Vascular Cell Adhesion Molecule-1, in Endothelial Biomedicine (Aird W C ed) pp 1058-1070, Cambridge University Press, New York). ICAM-1 is over-expressed on ECs during inflammation and is an anchor for leukocyte 132 integrins leukocyte function-associated antigen 1 (LFA-1) and macrophage differentiation antigen 1 (Mac-1) (Muro 2007). Through these interactions, ICAM-1 is involved in leukocyte firm adhesion to ECs, lateral crawling, and TEM (Phillipson et al.).

ICAM-1 engagement by WBCs mediates signaling involving $Ca^{2+}$, Src kinases and protein kinase C (PKC), Rho/ROCK-mediated formation of actin stress fibers, and cytoskeleton anchorage to the EC surface via binding of actin crosslinkers to the cytosolic domain of ICAM-1 (Hubbard A K et al. (2000) Free Radic Biol Med 28:1379-1386; Barreiro O., et al. (2002) J. Cell Biol. 157:1233-1245; Muro 2007). This is key in the formation of endothelial structures contributing to WBC TEM (Hubbard et al.; Barreiro et al. 2002; Yang L, et al. (2006) Circ Res 98:394-402; Muro 2007; van Buul J D, et al. (2007) J. Cell Biol. 178:1279-1293). For instance, ECs extend ICAM-1-rich microvilli projections that form a "cup" engulfing WBCs (endothelial docking structure), which depends on the cytosolic domain of ICAM-1 (Barreriro et al. 2002; Carman et al. 2004; Yang et al., 2005; Oh H-M, et al. (2007) Mol Biol Cell 18:2322-2335; van Buul et al. 2007). Prior to this, leukocytes extend podosomes into shallow invaginations in ECs in search for sites suitable for transcellular TEM (Carman C V, et al. (2007) Immunity 26:784-797). At these sites, ICAM-1-rich invaginations and vesicles from 200 nm to 1 µm in diameter coalesce, forming transcellular pores of up to 6 µm in diameter, through which leukocytes migrate transcellularly (Carman et al. 2007). Although there is consensus on the key role of ICAM-1 in WBC transcellular TEM, the nature of the transcellular pore and the vesicular pathway regulating its dynamic formation have not been established. Most works suggest a contribution of caveolar endocytosis (Millan et al. 2006; Marmon et al. 2009) and/or the related vesiculo-vacuolar organelle (Dvorak et al. 2001). Yet, other works have shown no association or partial association between ICAM-1 and caveolin-1 in structures that form during TEM (Carman et al. 2004; Carman et al. 2007).

It is unknown whether both routes of TEM serve similar functions, e.g., transmigration via the transcellular route may lead to more controlled transport between the bloodstream and the tissues, whereas the paracellular route involving opening between adjacent ECs may result in more profound leakage of blood components into tissues and edema. In this regard, it is plausible that the transcellular route serves as a surveillance mechanism and/or during physiological (controlled) inflammation, versus the paracellular route which may operate during inflammatory transmigration and/or pathological (uncontrolled) inflammation.

On the other hand, it is also possible that both routes operate as a surveillance mechanism and/or during the inflammatory response, yet they may be distinctly used by different types of WBCs (e.g., T or B lymphocytes, neutrophils, monocytes/macrophages, dendritic cells, natural killer cells, etc) and/or in different vascular beds of the body (pulmonary, brain, spleen, liver, skin, joints, the gastrointestinal tract, etc).

In any case, the knowledge of the mechanisms underlying interaction of WBC with the vascular endothelium as well as the processes regulating WBC migration across ECs are key for the development of strategies of prevention, diagnostic, and/or therapy of inflammatory conditions and a plethora of related maladies. In addition, similar mechanisms could be used to facilitate transport of diagnostic agents, therapeutics and their carriers to, into, and/or across ECs for translational applications.

Thus a need exists in the art for further understanding of the transcellular TEM pathway and development of methods for controlling and regulating transcellular TEM at a stage following initial engagement of an agent to the endothelium. Such methods would be useful in strategies to modulate inflammation as well as to provide controlled delivery of therapeutics and their carriers in the body.

SUMMARY OF THE INVENTION

The present invention relates to a method of regulating formation of engulfment or docking structures, uptake or transcellular transport of an agent, the method comprising administration of a regulator of CAM-mediated endocytosis or the sphingomyelin/ceramide pathway, wherein such administration is effective to regulate engulfment, uptake or transcellular transport of the agent.

In one aspect, the invention relates to a method of recovery of an inhibited pathway, the method comprising administration of a regulator of CAM-mediated endocytosis or the sphingomyelin/ceramide pathway, wherein such administration is effective to regulate engulfment, uptake or transcellular transport of the agent and wherein the inhibition is inhibition of engulfment, uptake or transcellular transport within a pathway selected from the group consisting of CAM-mediated endocytosis, sphingomyelin/ceramide pathway, phagocytosis, macropinocytosis, clathrin-mediated endocytosis and caveolar-mediated endocytosis.

In another aspect, the invention relates to a method of potentiating engulfment, uptake or transcellular migration of an agent, wherein the agent is complexed to a carrier targeted to a non-ICAM cell surface molecule or receptor, the method comprising administration of a regulator of CAM-mediated or the sphingomyelin/ceramide pathway, wherein such administration is effective to induce uptake of the agent and potentiation of transcellular transport of the agent.

In a still further aspect the invention relates to a method of modulating inflammation, comprising administration of a regulator of CAM-mediated endocytosis or the sphingomyelin/ceramide pathway, which is effective to regulate engulfment, uptake or transcellular transport of an agent of said inflammation.

Other aspects, features and embodiments of the invention will be more fully apparent from the ensuing disclosure and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
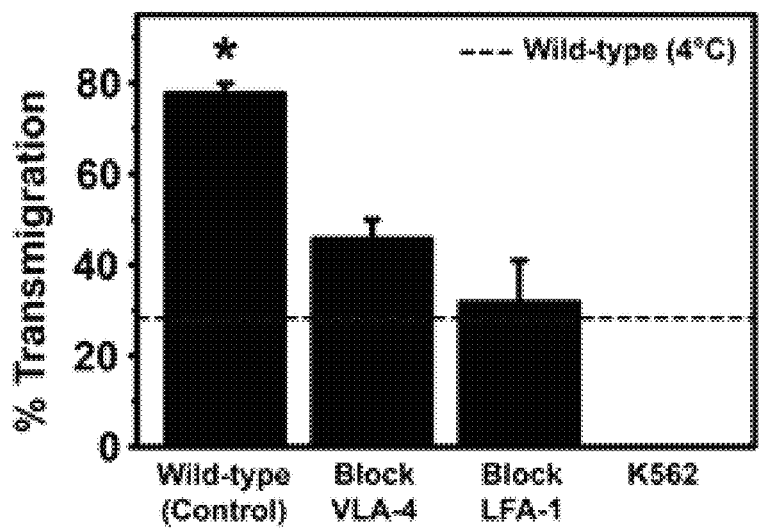
FIG. 1 is a graph of the model of Example 1, showing (A) transport of white blood cells (WBCs), lymphocytes (pre-blocked or not) and K562 cells across activated HUVEC monolayers and (B) transmigration of antibody-blocked WBCs in the presence (black bars) or absence (white bars) of HUVEC monolayer.
Figure 1:
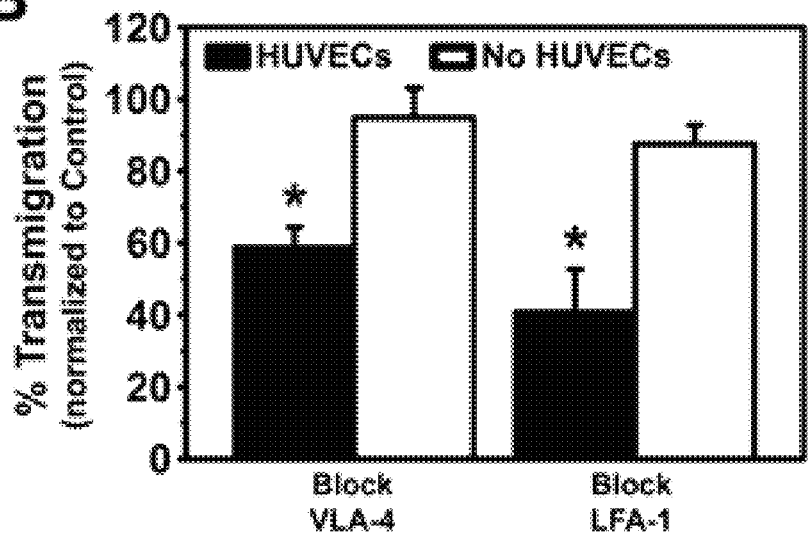

The present invention relates to methods of regulating transcellular transport of an agent and the involved engulfment or docking structures, and cellular uptake of such agent by manipulation of CAM-mediated pathways and/or the sphingomyelinase/ceramide pathway and the mechanisms involved in such pathways.

ICAM-1 is an immunoglobulin-family transmembrane glycoprotein that serves as an adhesive surface for leukocytes during inflammation (Yang et al., 2005; Muro et al. 2007; Rothlein R, et al. J Immunol (1986); 137:1270-4). It is constitutively expressed on diverse cell types, including, but not restricted to endothelial cells (EC) (Muro et al., 2007; Hopkins, A. M. et al. Adv Drug Deliv Rev 56 (2004): 763-778) and the expression of ICAM-1 is up-regulated in many pathologies (Muro et al., 2007; Rothlein et al., 1986; Hopkins et al., 2004; Hubbard et al., 2000).

Targeting ICAM-1 to block its adhesive function provides anti-inflammatory benefits (Takei, Y., et al. Transplant Proc 28 (1996): 11 03-1 105; Kavanaugh, A. F., et al. Arthritis Rheum 40 (1997): 849-853; Hallahan, D. E., et al. PNAS. 94 (1997): 6432-6437). In addition, ICAM-1 represents an attractive target for drug delivery to different sites in the body. For instance, antibodies to ICAM-1 are being explored as therapeutics and affinity carriers in cell cultures, animal models, and early clinical studies, where they have shown good safety (Muro et al., 2006; Garnacho, C. et al. JPET 325 (2008): 400-408; Garnacho C, et al. (2008) Blood 11 1:3024-3033; Muro S, et al. (2008) Mol Ther 16:1450-1458; Murciano, J. C. et al. Blood 101 (2003): 3977-3984; Muro et al., 2006; Villanueva F S, et al. Circulation 98 (1998): 1-5; Weller, G. E., et al. Ann Biomed Eng. 30 (2002): 101 2-1 01 9 Danilov, S. M. et al. Am J Physiol 280 (2001): L1335-L1347; Sakhalkar, et al. PNAS 100 (2003): 15895-1 5900; Rossin, et al. J. Nucl. Med. 49, 1 (2008): 103-111; Muro S, et al. (2005) Blood 105:650-658). The present inventors have also designed short peptides derived from a natural protein present in the human circulation and peptides identified by phage-display, all of which serve as ICAM-1 targeting molecules to provide efficient and specific binding of therapeutic agents and drug delivery systems to ICAM-1 in both mice and human cells (International Publication No. WO 2010/141879; U.S. Provisional Patent Applications 61/220,404 and 61/184,657).

The involvement of ICAM-1 in leukocyte TEM via both the paracellular and transcellular routes is known, but its role and the modulation of this pathway are not completely understood. As compared to other endothelial adhesion molecules, ICAM-1 plays a key role in transcellular TEM (Barreiro et al., 2002; Yang et al., 2005; Millan et al., 2006; Ley et al., 2007; Oh P, et al. (2007) Nat Biotechnol 25:327-337). Endothelial endocytic vesicles that form in this process coalesce, generating a transcellular pore through which WBCs transmigrate transcellularly (Carman et al. 2004; Carman et al. 2007). Hence, if ICAM-1 was involved in the regulation of such transcellular TEM pathway, binding to ICAM-1 (ICAM-1 engagement) would contribute to inducing formation of engulfment or docking structures, endocytic vesicles, and transcellular transport pores in ECs. Specific engagement of endothelial ICAM-1 by other "ligands" (protein conjugates and polymer particles coated with antibodies to ICAM-1 (anti-ICAM) used for drug delivery) is sufficient to elicit formation of endocytic vesicles in cytokine activated ECs (Muro et al., 2003; Muro et al., 2006; Muro et al., 2008).

Cell adhesion molecule (CAM)-mediated endocytosis, distinct from clathrin- or caveolae-mediated endocytosis, macropinocytosis, or phagocytosis (Muro et al., 2003; Muro et al., 2006; Muro et al., 2008), results in cytoskeletal rearrangement with formation of actin stress fibers (Muro et al., 2003; Muro et al., 2006; Muro et al., 2008). During CAM-mediated endocytosis, ICAM-1 interacts with the $Na^+/H^+$ exchanger NHE1, a molecule which acts as a crosslinker of actin filaments to the cytosolic domain of ICAM-1 (Denker, S P, et al. (2000) Mol Cell 6:1425-1436; Muro et al., 2006).

Nevertheless, the pathway previously thought to contribute to ICAM-1-mediated regulation of leukocyte TEM was the caveolar pathway (Millan et al., 2006; Marmon et al., 2009) and/or the associated vesiculo-vacuolar organelle (Dvorak et al., 2001). However, formation of endocytic vesicles upon engagement of ICAM-1 is mediated by CAM-mediated endocytosis (Muro et al., 2003; Muro et al., 2006; Muro et al., 2008), which is unrelated to said caveolar-mediated endocytosis or the related vesiculo-vacuolar organelle (Muro et al., 2003; Muro et al., 2006; Muro et al., 2008). Formation of endocytic vesicles upon ICAM-1 engagement by anti-ICAM particles is not affected by filipin, a drug that sequesters cholesterol in the plasma membrane of cells and inhibits caveolar-mediated pathways (Muro et al., 2006). Also, anti-ICAM beads and related vesicles do not co-localize with cholera toxin B, a molecule known to bind to ganglioside GM1 in lipid raft-related regions of the plasmalemma, followed by internalization within cells via caveolar- and (alternatively) clathrin-mediated pathways. Indeed, in addition to the caveolar pathway, none of the other classical endocytic pathways which naturally operate in cells in the body, such as said clathrin-mediated endocytosis, macropinocytosis or phagocytosis, is related to the formation of endocytic vesicles via ICAM-1 engagement (Muro et al., 2003; Muro et al., 2006; Muro et al., 2008).

In addition, transmigration of WBCs across the endothelium is believed to require active regulation by leukocytes (Nourshargh et al 2010). Evidence shows that the ability of leukocytes to migrate laterally along the endothelial surface is important in the decision between paracellular versus transcellular TEM (Phillipson et al. 2006, Gerard A, et al. (2009) Blood 11 3:6138-61 47), as WBCs probe for sites suitable for transmigration (Carman et al., 2004). In contrast to the active role of WBCs interacting with endothelial cells, CAM-mediated endocytosis has only been associated with engagement of endothelial ICAM-1 by "artificial" and "inert" objects, such as protein conjugates and polymer particles targeted to ICAM-1 via anti-ICAM antibodies or peptides (Muro et al., 2003; Muro et al., 2006; Muro et al., 2008), but it has not been observed in any of the multiple previous works looking at the interaction of WBCs with endothelial cells. CAM-mediated endocytosis has been also shown to be induced in the case of engagement of another endothelial molecule, platelet-endothelial cell adhesion molecule 1 (PECAM-1), by anti-PECAM conjugates and polymer particles (Muro et al., 2006). Yet, only ICAM-1, but not PECAM-1, has been shown to be necessary for transcellular TEM of leukocytes.

Also, endocytosis induced by "artificial" and "inert" anti-ICAM conjugates or polymer particles or beads has not been shown to result in endocytic vesicles that coalesce to form transendothelial pores but rather to result in transport of individual vesicles to either plasma membrane recycling pathways (in rare instances) or (in most instances) to transport to endosomes and lysosomes (Muro et al., 2003, Muro et al., 2005; Muro et al., 2006).

Thus, the role of CAM-mediated endocytosis on WBC TEM, particularly via the transcellular route, was hardly predictable and somewhat unlikely. Yet, signaling associated to CAM-endocytosis is somewhat similar to leukocytes: $Ca^{2+}$ signaling, activation of Src, PKC, and Rho/ROCK, and formation of actin stress fibers (Muro et al., 2003; Muro et al., 2006; Muro et al., 2008). Also, ECs endocytose anti-ICAM beads of various shapes and sizes, whose dimensions range from a hundred nanometers to several micrometers, both in cell culture and in vivo (Muro et al., 2003; Muro et al., 2005; Muro et al., 2006; Muro et al., 2008) and this occurs without opening of the endothelial junctions (Muro et al., 2005; Muro et al., 2008). Therefore, the present inventors explored the association among these phenomena in order to more fully understand transcellular transport.

Using anti-ICAM beads, peripheral blood leukocytes and molecular, cellular and in vivo tools, as detailed in the Examples below, an unexpected role for the sphingomyelin/ceramide pathway commonly underlying and connecting these processes was found. The data presented herein demonstrate that formation of plasmalemma engulfing structures, invaginations and coalescing vesicles, as well as upstream signaling and cytoskeletal restructuring driving CAM-mediated endocytosis of "artificial" ICAM-1 ligands (e.g., anti-ICAM beads) is indeed reminiscent of the events elicited during ICAM-1 engagement by WBCs transmigrating across ECs and contribute to transcellular TEM.

Therefore in one aspect, the invention relates to methods of regulating transcellular TEM of agents, involving control of such CAM-mediated endocytosis and sphingomyelin/ceramide pathway.

Such regulation can be utilized in myriad ways to control cellular uptake, internalization, transport, delivery and/or arrest of agents. Further uses of the regulation include control of pathogens that bind to ICAM-1, which may invade within cells or be transported across cells.

In a particular embodiment the invention relates to methods of regulating transcellular transport of agents, which further provides the ability to control the inflammatory interaction of leukocytes and the endothelium and to regulate delivery of therapeutics in the body via ICAM-1 targeting strategies, as well as via binding to other cell surface markers while providing elements of the CAM- or sphingomyelin/ceramide pathways.

A method of regulating formation of engulfment or docking structures, uptake and/or transcellular transport of an agent, the method comprising administration of a regulator of CAM-mediated endocytosis or the sphingomyelin/ceramide pathway, wherein such administration is effective to regulate engulfment, uptake or transcellular transport of the agent.

Initially, the effect of disrupting lipid domains (which have been associated to caveolar pathways) or CAM-mediated endocytosis on leukocyte transmigration across endothelial cells was examined. A model for examination of transmigration of white blood cells across endothelial monolayers was developed as described in Example 1. As described in detail in Example 1 and shown in the results presented in FIG. 2, it was demonstrated that both lipid domains and CAM-mediated endocytosis are involved in WBC transmigration, but caveolae-mediated pathways are not.

Example 2 provides a model of paracellular versus transcellular transmigration of white blood cells, which was used to examine the role of lipid domains and CAM-mediated endocytosis in paracellular versus transcellular diapedesis of leukocytes. The results of Example 2 suggest a main role for lipid domains and CAM-mediated endocytosis, and not caveolae-related pathways, in transcellular TEM versus the paracellular route.

Example 3 documents the evaluation of the association of lipid domains and the sphingomyelin/ceramide pathway to endothelial docking structures induced by ICAM-1 engagement. Endothelial engulfment of WBCs at lipid raft-like, ICAM-1-rich docking structures occurs in association with WBC adhesion to the endothelium and TEM via transcellular pores (Barreiro et al., 2002; Carman and Springer 2004; Oh et al., 2007; van Buul et al., 2007). However, experiments using WBCs involve engagement of multiple adhesion molecules on the endothelial plasmalemma. Example 3 demonstrates correlation of ICAM-1 specifically with lipid domains at the EC surface and formation of engulfing or docking structures.

Figure 2:
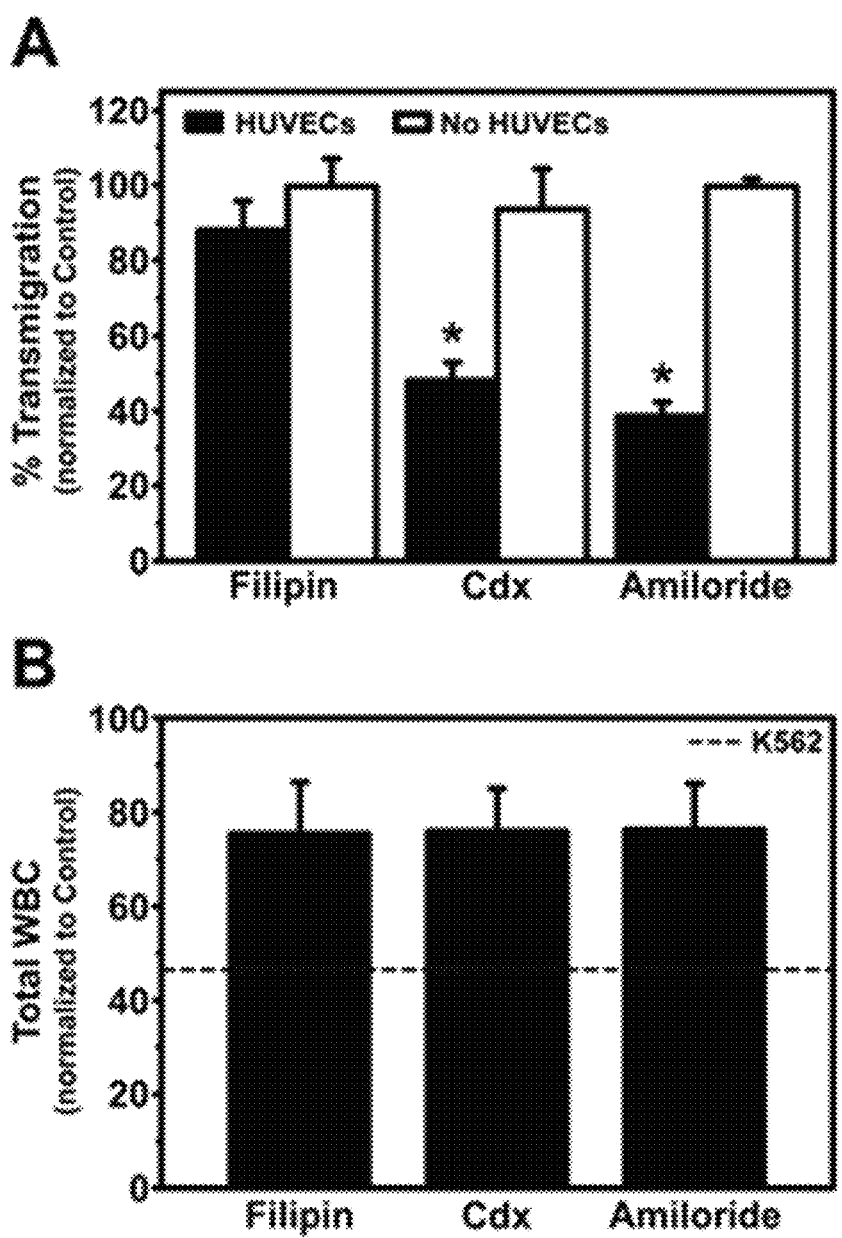
FIG. 2 is a graph of the endothelial transmigration (A) and binding (B) of WBCs in the presence or absence of filipin, methyl-β-cyclodextrin (Cdx) or amiloride.
Figure 4:
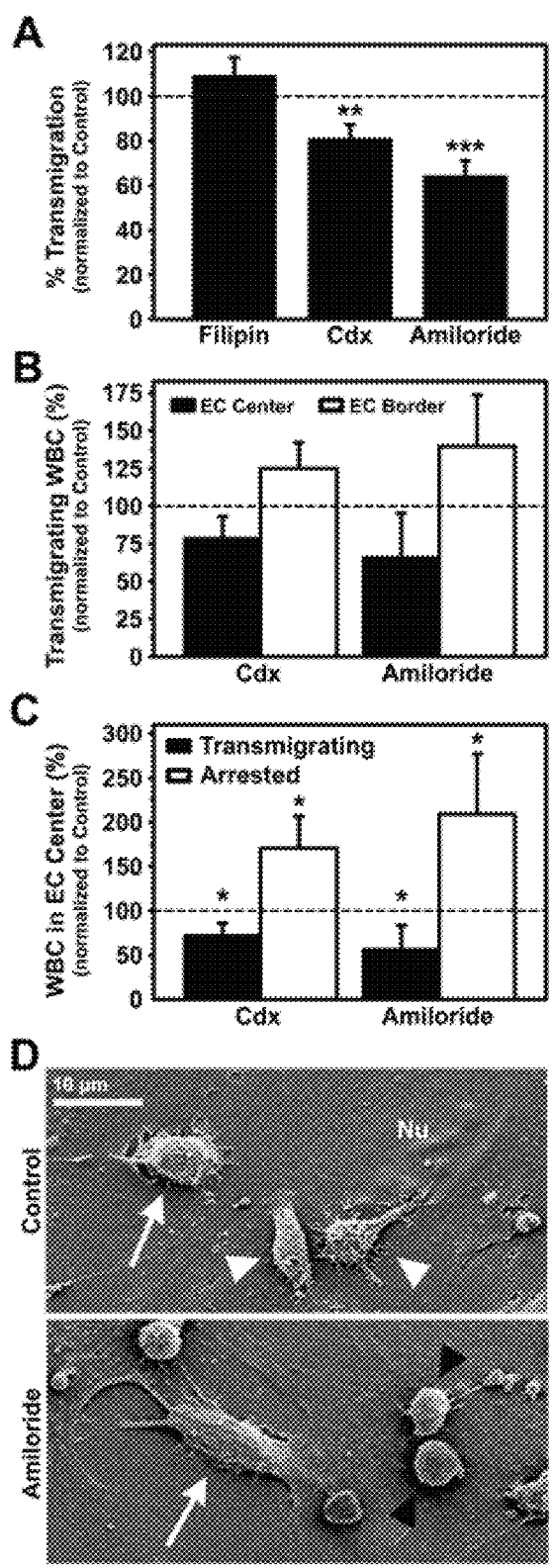
FIG. 4 provides graphs of activated white blood cells as described in Example 2, showing (A) transmigration as measured by projecting podosomes into/under HUVECs; (B) location of transmigrated WBCs; (C) comparison of transmigrating and arrested WBCs; and (D) electron micrographs showing effect of amiloride on distribution of WBC transmigration events.

Example 4 demonstrates that the typical lipid raft-domain components cholesterol, sphingomyelin and ganglioside GM1 were enriched in areas of engulfment of anti-ICAM beads in Example 3, mimicking endothelial docking structures (ring-shaped fluorescent regions in FIG. 6A). The results of Example 4 correlate well with the findings presented in FIGS. 2 and 4, showing that disruption of lipid domains and CAM-mediated pathway affect transcellular TEM and indicating that ICAM-1 engagement may be sufficient to induce endothelial docking structures at these lipid domains.

Since hydrolysis of sphingomyelin into ceramide contributes to formation of large lipid domains and this pathway is associated to modulation of the plasmalemma plasticity and cytoskeletal signaling (Holopainen J M, et al. (1998) Biochemistry 37: 17562-1 7570; Zha X, et al. (1998) J. Cell Biol.; 140(1):39-47; Holopainen J M, et al. (2000) Biophys J 78:830-838; Zeidan Y H, et al. (2008) J. Cell Biol. 181:335-350), features required during WBC TEM, ceramide was tested for at regions of ICAM-1 engagement by anti-ICAM beads.

As described in Example 4 and shown in FIG. 6C i, iv, ceramide also increased (3.5±0.01-fold) at these regions over adjacent areas, which was impaired by EIPA (35.6% decrease; FIG. 6Cii,iv), an amiloride derivative that more specifically inhibits NHE1 involved in CAM-mediated endocytosis (Muro et al., 2003; Muro S, et al. (2006) Am J Physiol Lung Cell MolPhysiol 290:L809-817). As such, NHE1 was identified as having a critical function in particle internalization and as a possible connector of the CAM-mediated pathway to sphingomyelin/ceramide signaling.

To investigate this connection further, the potential recruitment of acid sphingomyelinase during formation of endothelial docking structures induced by ICAM-1 engagement was examined, as described in Example 5. Contribution of the sphingomyelin/ceramide pathway to formation of endothelial docking structures and WBC TEM may require sphingomyelinase activity. Given that NHE1 provides acidification at the extracellular side of the plasmalemma (Bourguignon L Y W, et al. (2004) J Biol Chem 279:26991-27007), the present inventors theorized that acid sphingomyelinase (ASM), a lysosomal enzyme that can be secreted (Jenkins R W, (2009) Cell Signal 21:836-846), is involved in ceramide generation at these regions.

The results of Example 5 support the assertion that ASM secretion is associated with the CAM-mediated pathway. Accordingly, Example 6 was performed to confirm this by evaluating the effect of impairing acid sphingomyelinase on CAM-mediated endocytosis. Ceramide production by ASM at sites of ICAM-1 engagement where NHE1 acidifies the milieu may provide plasmalemma plasticity (and likely cytoskeleton signaling; Holopainen et al., 1998; Zha et al., 1998; Holpainen et al., 2000; Zeidan et al., 2008) required by endothelial docking-like structures involved in engulfment of micron-sized objects and WBCs, which the present inventors attribute to the CAM-mediated pathway, rather than caveolae-mediated pathways.

Furthermore, an in vivo mouse model detailed in Example 6 confirmed that engulfment leading to endocytosis of anti-ICAM beads by ECs was inhibited in ASM$^{-/-}$ mice.

Example 7 provides an examination of the role of acid sphingomyelinase in leukocyte transcellular transmigration. The inventors had hypothesized that ASM was involved not only in the formation of CAM-mediated vesicles but also fusion of said vesicles into larger structures, similar to formation of ICAM-1-rich invaginations and vesicles that coalesce into transmigration pores. As such, the example looked for ASM to appear at areas of WBC migration across ECs and its inhibition to affect transcellular TEM.

The results of Example 7 support a concerted role for sphingomyelin/ceramide signaling and NHE1-dependent CAM-mediated endocytosis induced upon ICAM-1 engagement at the EC surface, in transcellular TEM. This model is consistent with findings obtained using WBCs and specific ICAM-1 engagement by anti-ICAM beads, pharmacological inhibitors and genetically modified models, cell cultures and in vivo systems.

Taken together, the results reported herein support a model for transcellular TEM that includes, but is not limited to, engagement of ICAM-1 in lipid domains enriched in sphingomyelin, which induces secretion of acid sphingomyelinase (ASM) from intracellular compartments to these areas of the endothelial plasma membrane. At these sites, engaged ICAM-1 forms a complex with NHE1, which results in local acidification, sphingomyelin hydrolysis by secreted ASM, and local production of ceramide. This signal leads to actin polymerization and cytoskeleton remodeling, stabilizes the engagement platform by restricting molecular diffusion and providing cytoskeletal anchorage, regulates membrane deformability, and favors dynamic formation of CAM-mediated endocytic vesicles, which occurs at sites of leukocyte-podosome sampling in search from sites suitable for transcellular TEM. Finally, vesicular fusion mediated through sphingomyelin/ceramide signaling at this interface results in transmigration pores.

The model of transcellular TEM presented herein explains particular molecular and cellular features required for such events to take place. For instance, the ion exchange activity of NHE1 regulates the elasticity of the endothelial apical surface (Hillebrand U, et al. (2006) Cardiovasc Res 69:916-924), in agreement with high permissibility of CAM-mediated endocytosis for engulfment and uptake of large micron-sized objects in vitro and in vivo (Muro et al., 2008). This is in contrast to the caveolar and clathrin pathways, shown to be rather restricted regarding the size of "ligands" that can accommodate to typical caveolar vesicles (Oh et al., 2007).

Such deformability properties of CAM endocytosis, which can be exploited for transport of drug carriers into and across cells, would suitably adapt for formation of large endothelial docking structures, the wide range of sizes exhibited by the invasive podosomes that leukocytes extend into ECs during TEM, and formation of the transcellular pore (Carman et al., 2004; Carman et al., 2007). Also in the context of CAM-mediated endocytosis and WBC TEM, diffusion of molecules in the plasmalemma must be temporarily reduced in areas of binding to ICAM-1, to permit formation of engagement and signaling platforms, and to anchor the cytoskeleton.

The level of deformability required to engulf large objects and cells by endothelial docking structures progressing into transmigration pores must also relate to a particular lipid composition of the plasmalemma. As shown here, such domains seem to be related also to CAM-mediated pathway, and are associated to induction of sphingomyelin/ceramide signaling upon ICAM-1 engagement at the EC plasmalemma. As observed in other systems, ceramide confers particular properties to the membrane environment depending on the ratio of raft components (Rotolo J A, et al. (2009) Blood 11 4:3693-3706; Silva L C, et al. (2009) Biophys J 96:3210-3222), e.g., it can promote the formation of large lipid domains (Holopainen et al., 1998; Holopainen et al., 2000) or displace lipid domain constituents to affect membrane function (Zeidan et al., 2008).

Ceramide production by ASM at the outer leaflet of the plasma membrane modifies its curvature and results in vesiculization (Zha et al., 1998; Holopainen et al., 2000; Tam C, et al. (2010) J. Cell Biol. 189:1027-1038), as well as cytoskeletal rearrangements (Zeidan et al., 2008). These events downstream of the sphingomyelin/ceramide pathway could contribute to formation of large micron-sized vesicles in the absence of clathrin or caveolin coats, as observed in CAM-mediated endocytosis (Muro et al., 2003; Muro et al., 2008) (Table 1). In addition, ceramide production by ASM is associated with vesicular fusion (Utermohlen O. et al. Immunobiology 21 3:307-314), which could contribute to dynamic formation of transcellular pores from vesicles forming via CAM-mediated pathway. This agrees with the observation that in ASM$^{-/-}$ mice, the beads that were internalized by ECs were found individually in vesicles, while in control mice, vesicular fusion resulted in the accumulation of several beads within larger compartments (Table 1).

Given that ICAM-1 interacts with NHE1 upon ICAM-1 engagement (Muro et al., 2006), and due to the directionality of NHE1 ion exchange (Na' influx/H' efflux; Denker et al., 2000; Bourguignon et al., 2004), it is expected that ion transport activity of NHE1 will locally acidify ICAM-1 engagement regions, creating a confined acidic microenvironment. A similar function of NHE1 has been shown in the context of other pH-sensitive enzymes (Bourguignon et al., 2004). Secreted ASM, whose pK, is acidic (Jenkins et al., 2009), would only be able to efficiently hydrolyze sphingomyelin into ceramide at NHE1-enriched, ICAM-1 engagement regions. This provides a suitable explanation for how an acidic enzyme can elicit activity at the otherwise neutral extracellular environment and may also contribute to understanding the mechanism by which ECs regulate ceramide production with spatial precision. It is also possible that other sphingomyelinases (e.g., neutral enzymes) may overlap with this function.

The discovery of both of the sphingomyelin/ceramide pathway and CAM-mediated endocytosis as key contributors to leukocyte transmigration, particularly via, but not restricted to, the transcellular route, provides necessary further understanding of the transcellular TEM pathway and provided an important step in the development of methods for controlling and regulating transcellular TEM at a stage following initial engagement of an agent to the endothelium. As a result of the discoveries reported herein with regard to the mechanisms of leukocyte transmigration, the present invention relates to methods of utilizing such mechanisms to regulate transendothelial migration.

Further, varied genetic, biotechnological, or pharmacological (among other) interventions to regulate (potentiate or inhibit) signaling induced by ICAM-1, the action of NHE1, ASM or other sphingomyelinases, ceramide production by other methods are provided to promote transmigration of leukocytes (e.g., to combat infection,) or to inhibit such transmigration (e.g., to control inflammation). Such methods are useful to impact a plethora of diseases in which inflammation plays a role, including but not restricted to inflammatory and autoimmune conditions (rheumatoid arthritis, psoriasis, ulcerative colitis, Crohn disease, etc.), infections and septic shock, ischemia-reperfusion injury, atherosclerosis and thrombosis, metabolic and genetic disorders, asthma and acute lung injury, cancer and tumor metastasis, and many others.

Still further, given that promotion of ceramide production in the plasmalemma (demonstrated herein via a showing of ICAM-1 engagement and the CAM-mediated pathway activating ASM activity) was shown to provide optimal conditions for internalization within cells and/or transport across cells, the discovery of the sphingomyelin/ceramide pathway and CAM-mediated endocytosis as key contributors to transmigration are broadly applied to support new strategies to control and facilitate body transport of diagnostic and therapeutic agents, and their targeting molecules and carriers. Methods of the invention include intracellular delivery or delivery across cellular barriers, such as the blood-brain barrier in the central nervous system, the blood-air barrier in the lungs, the epithelial barrier in the gastrointestinal tract, penetrability into tissues and organ, and the like.

Therefore, in one embodiment the invention relates to a method of regulating transcellular transendothelial migration of an agent, the method comprising administration of a regulator of CAM-mediated endocytosis or the sphingomyelin/ceramide pathway, wherein such administration is effective to regulate transcellular TEM of the agent.

As used herein, a "regulator" can be administered to regulate the CAM-mediated endocytosis or the sphingomyelin/ceramide pathway. By "regulation" or "regulating" of CAM-mediated endocytosis or the sphingomyelin/ceramide pathway includes any of controlling, managing, adjusting, directing, manipulating or modulating CAM-mediated endocytosis or the sphingomyelin/ceramide pathway. Regulators of CAM-mediated endocytosis or the sphingomyelin/ceramide pathway according to methods of the invention are effective after ICAM-1 engagement of the agent. Regulators of the invention target steps of engulfment or formation of docking structures, uptake by cells and formation of vesicles, as well as pore opening and transcellular TEM or transcytosis.

Administration of a regulator may include actual administration of the regulator in vitro or in vivo to a system or patient in need of such administration. Administration may be by any suitable administration mechanism that provides effective levels of the regulator to the endothelium. Any suitable administrative routes that are compatible with the selected regulator may be employed. Administration methods of regulators described herein include, but are not limited to, parenteral administration, intraperitoneal (i.p.) administration, intravenous (i.v.) administration, intraarterial (i.a.) administration, intradermal (i.d.) administration, intramuscular (i.m.) administration, and subcutaneous (sc) administration.

Administration of a regulator may also include indirect administration such as induction or inhibition of a regulator within the subject system or patient.

As exemplified herein, regulators may include, but are not limited to, NHE1, sphingomyelinases, acid sphingomyelinase and ceramide. Further regulators useful in methods of the invention may include, but are not limited to, proteins affecting the CAM-mediated pathway, ICAM-1, lipids affecting the CAM-mediated pathway, sphingomyelin, and ceramidases.

Acid sphingomyelinase (ASM), other sphingomyelinases, and NHE1 are proteins that may be directly administered to regulate CAM-mediated endocytosis or the sphingomyelin/ceramide pathway. Such proteins may be obtained by any means known, from any known source, such as from organisms, humans or recombinantly produced. ASM, other sphingomyelinases, and NHE1 may also be administered by indirect means, such as by inducement of expression or over-expression of these proteins within the subject system or patient. In one embodiment, methods of the invention may include gene therapy to induce expression of a regulator of the CAM-mediated endocytosis or the sphingomyelin/ceramide pathway. In another embodiment, methods of the invention may include administration of an activator that activates production of the regulator. Insulin is an activator of NHE1, and other activators include molecules that activate PKC (e.g., PMA, bryostatin) and Rho, among others. Activators of sphingomyelinases are saposins, DC-SIGN, OxPAPC, neutral sphingomyelinase (N-SMase) activation associated factor or NSMAF, molecules that activate PKC, and the like.

Regulators such as ASM, other sphingomyelinases, and NHE1 may also be inhibited by known methods, such as use of siRNA to knock-down expression of these proteins or by using blocking antibodies. Induction may also be achieved by administration of inhibiting compounds. Inhibitors of NHE1 may include, but are not limited to amiloride and derivatives like 5'-(N-ethyl-N-isopropyl)amiloride (EIPA), and benzoylguanidine (Hoechst type inhibitor (HOE))-type compounds. Inhibitors of ASM may include, but are not limited to imipramine, its derivatives like desipramine, SR33557, D609, and others. Inhibitors of sphingmyelinases may include, but are not limited to scyphostatin, 3,4-Dichloroisocoumarin Chlorpromazine, Hydrochloride Fumonisin $B_1$, *Fusarium moniliforme* Gentamycin Sulfate Manumycin A, *Streptomyces parvulus* N-SMase Inhibitor, GW4869 and $N^{\alpha}$-Tosyl-Phe Chloromethyl Ketone. Such inhibition is contemplated within administration of a regulator.

Additional regulators may include, but are not limited to lipids such as sphingomyelin and ceramide. As discussed above with regard to protein regulators, lipid regulators may be administered directly, such as by exogenous application to a system or subject in need of a method of the invention or may be administered indirectly, such as by modulation of enzymes involved in the mechanisms of synthesis or degradation routes of these lipids. In one embodiment, activation or inhibition of ceramidases would degrade ceramide or inhibit its degradation, respectively, and thereby impact the presence of ceramide in the pathway.

Regulators of the invention are useful for regulation of CAM-mediated endocytosis or the sphingomyelin/ceramide pathway. By such regulation, the engulfment, uptake within vesicles, and/or transcellular transport of an agent can be affected.

In one embodiment of the methods of the invention, the regulator inhibits CAM-mediated endocytosis and inhibits engulfment, uptake within cells, and/or transcellular TEM or transport of the agent. In another embodiment of the methods of the invention, the regulator induces CAM-mediated endocytosis and induces engulfment, uptake within cells, and/or transcellular TEM or transport of the agent. In still another embodiment the regulator inhibits the sphingomyelin/ceramide pathway and inhibits engulfment, uptake within cells, and/or transcellular TEM or transport of the agent. In a further embodiment, the regulator induces the sphingomyelin/ceramide pathway and induces engulfment, uptake within cells, and transcellular TEM or transport of the agent. The invention further contemplates combined effects on CAM-mediated endocytosis and the sphingomyelin/ceramide pathway.

Agents useful in methods of the invention may include, but are not limited to, autologous or foreign white blood cells, leukocytes, pathogens, drugs, natural and/or artificial molecules and/or objects including, but not limited to, research, analytical or molecular probes, diagnostic agents, therapeutic agents, biologically active agents, research agents, analytical agents, imaging agents, monitoring agents, enzymes proteins, hormones, lipids, sugars, nucleic acids, lipoproteins, and chemicals.

Agents may be present alone or may be complexed to an additional moiety. As used herein, "complexed" refers to the association between the agent and the moiety, including binding, fusing, linking, coupling, connecting or otherwise associating the agent and the additional moiety. The resulting complexes may be a single entity, such as a fusion protein or may result from coupling via absorption mechanisms, by chemical modification, through a crosslinker molecule, or via adaptor molecules. Any such complexing is contemplated in methods of the invention.

Additional moieties for complexing to the agent may include, but are not limited to, targeting moieties, cargo, carriers, delivery vehicles, and combinations thereof.

Where the agent is complexed to a targeting moiety, such may include, but is not limited to, a polypeptide such as an antibody, antibody fragment, single chain Fv derivative, humanized antibody, natural protein, peptide, or any other natural, recombinant or synthetic affinity moiety recognizing CAMs. In other embodiments the targeting moiety targets a cell surface marker other than ICAM-1, including, but not limited to, receptors associated to other mechanisms of endocytosis and transport across cells, including but not restricted to phagocytosis, macropinocytosis, clathrin-mediated transport and caveolar-mediated transport. In one such embodiment the non-ICAM receptor is M6PR.

Where the agent is complexed to cargo, the cargo may include, but is not limited to a cell or modified cell, reporter probe, biosensor, marker, antibody, peptide or protein, enzyme, ligand, genetic material (DNA- and RNA-based), drug or chemical, imaging or therapeutic agent, or any combination of the above. Cargo included in methods of the invention may be directly delivered by the targeting moiety or may be additionally assisted by a delivery vehicle or carrier.

The invention provides a new strategy to regulate transcellular TEM and to thereby regulate interaction of leukocytes with the endothelium and transport thereof and also to regulate transport of therapeutics and their carriers in the body, and, still further, to generally regulate cellular uptake of agents within cells and across cells via the transcellular pathway, supporting multiple basic, research, and translational applications. The regulatory methods of the invention are broadly applicable to methods such as, but not limited to, modulation of inflammation, pathogen invasion and drug delivery.

In applicability to modulation of inflammation, the identification of pathways subject to regulation permits control of transcellular TEM. The transcellular TEM pathway can selectively be upregulated to promote transmigration or downregulated to inhibit or avoid transmigration. Further, the methods of the invention can be used to shift between transcellular and paracellular transmigration pathways. In paracellular TEM, the "leaky vasculature" of the open junctions between cells can permit entrance of undesired substance, such as red blood cells, proteins and the like. Accordingly, in some situations it is desirable to favor transcellular TEM. However, in other situations it is desirable to disfavor transcellular TEM.

In other applications, the methods of the invention are useful in the delivery of agents. Agents may be targeted to a surface marker (e.g. ICAM-1 or a receptor associated to classical vesicular transport, including but not restricted to M6PR) and engulfment, uptake by cells, or transcellular transport downregulated, such that the agent remains immobilized on the surface of the EC. As such the agent is anchored on the EC. Additionally, agents may be targeted to a surface receptor and engulfment, uptake by cells, or transcellular transport upregulated, such that the transport of the agent is controlled. Such steps of immobilization and transport may also be combined through use of multiple regulators and/or timing of regulators, such that an agent may be initially immobilized, then transported via transcellular TEM at an appropriate time to a desired locale. The methods of the invention are therefore applicable to promote or avoid entrance of an agent into endothelial cells and/or across the endothelial lining.

Still further, the invention relates to applicability of methods of the invention to control of pathogenic invasion via ICAM-1. Where an agent is a pathogen, the engulfment, uptake within cells, and/or transcellular transport pathway can selectively be upregulated to promote uptake and transmigration or downregulated to inhibit or avoid uptake or transmigration. Promotion of transmigration can be utilized to promote or otherwise include transport of the pathogens to lysosomes and/or vacuoles for subsequent degradation and protection of the cells in the body against infection. Inhibition of transmigration can be used to prevent pathogenic cellular invasion.

Further embodiments of the invention provide applicability of the methods of the invention to drug delivery systems. In one embodiment the agent is a drug and such agent is complexed to an imaging agent. Promotion of uptake within cells and/or transcellular transport can be utilized for targeted delivery of the drug to the cells and/or tissues.

In a still further embodiment the invention relates to recovery of the action of an inhibited CAM-mediated uptake and transcellular transport pathway. In another embodiment, the invention relates to enhancement of uptake and/or transcellular transport when using targeting to other cell surface markers and pathways while providing exogenously elements of the CAM- or sphingomyelin/ceramide pathways. The method relates to a method of recovery of an inhibited pathway, the method comprising administration of a regulator of CAM-mediated endocytosis or the sphingomyelin/ceramide pathway, wherein such administration is effective to regulate engulfment, uptake or transcellular transport of the agent and wherein the inhibition is inhibition of engulfment, uptake or transcellular transport within a pathway selected from the group consisting of CAM-mediated endocytosis, sphingomyelin/ceramide pathway, phagocytosis, macropinocytosis, clathrin-mediated endocytosis and caveolar-mediated endocytosis.

Example 8 demonstrates that even in $ASM^{-/-}$ ECs, endocytosis of very large objects (anti-ICAM particles about 5 micrometers in diameter) can be achieved by coupling ASM, as a regulator, to said objects as agents (which in this case improved endocytosis from 7% to 25%). By providing acid sphingomyelinase exogenously to cells where the ICAM pathway has been inhibited, recovery of the pathway action is observed.

Potentially, similar outcomes could be obtained using targeting to other cell receptors even if they do not activate acidification via NHE1, for instance, by using neutral sphingomyelinases instead of acidic counterparts.

In a still further embodiment the invention relates to a method of potentiating cellular engulfment, uptake and/or transcellular transport of an agent, where the agent is complexed to a carrier targeted to a non-ICAM cell surface molecule or receptor, the method comprising administration of a regulator of CAM-mediated endocytosis or the sphingomyelin/ceramide pathway, wherein such administration is effective to induce uptake of the agent and potentiation of transcellular transport of the complex.

Figure 16:
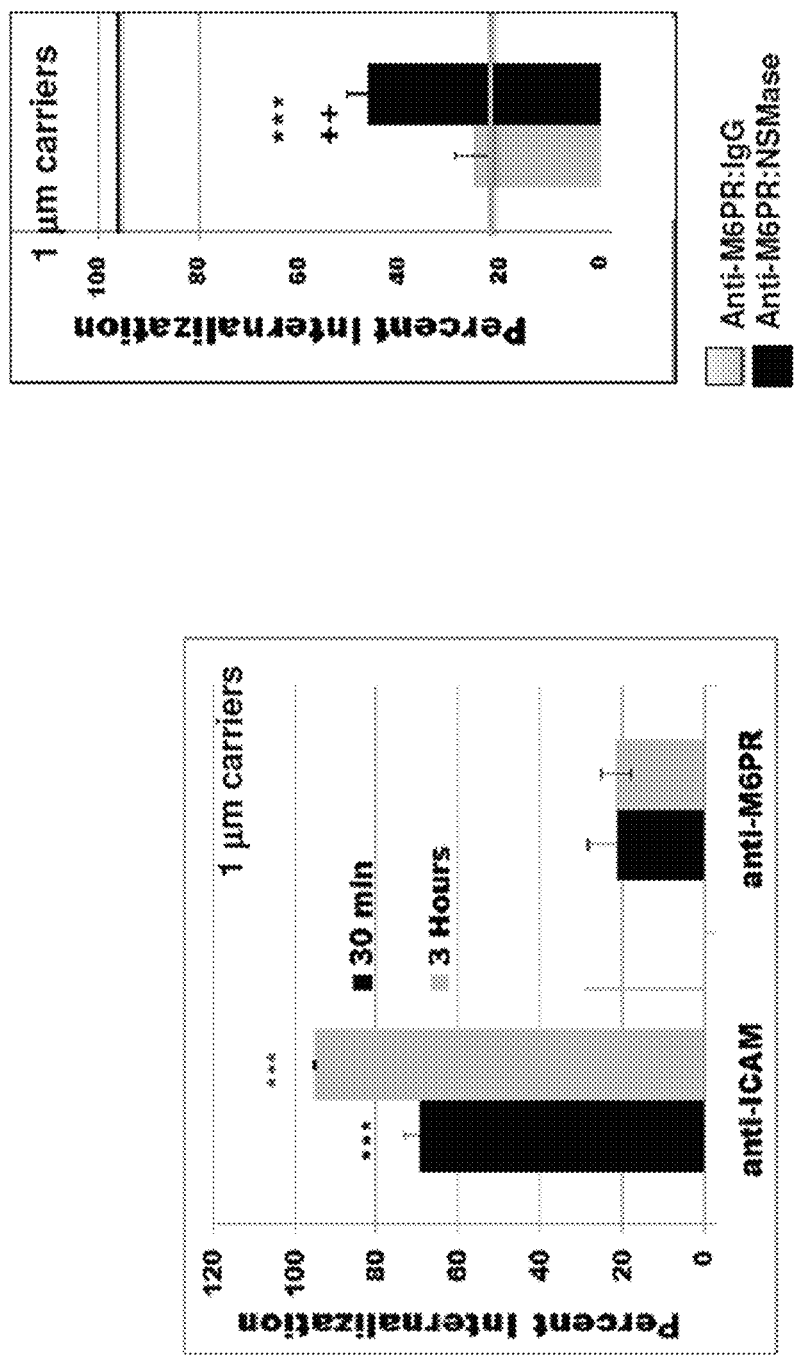
FIG. 16 provides graphs showing the effects of coupling sphingomyelinases to particles targeted to cell surface markers other than ICAM-1, e.g., mannose-6-phosphate receptor (M6PR), where (A) provides percent internalization of said particles prior to coupling to M6PR and in comparison to anti-ICAM particles, and (B) provides data regarding the uptake of M6PR targeted carriers after coupling to neutral sphingomyelinase to the surface of the carriers.

As an example of one embodiment of the invention, FIG. 16 demonstrates enhancement of cell uptake of drug delivery carriers by sphingomyelinases. FIG. 16A illustrates the observed percent internalization into human vascular endothelial cells (HUVECs) at 30 minutes or 3 hours, of model 1 micrometer diameter polymer (polystyrene) drug carriers, targeted to either ICAM-1 or mannose-6-phosphate receptor (M6PR). It is seen that the ICAM-1-mediated pathway results in more effective uptake of carriers by cells, since ICAM-1 mediates uptake via cell adhesion molecule (CAM) endocytosis, which associates to the sphingomyelin/ceramide pathway, where acid sphingomyelinase regulates formation of plasma membrane engulfment structures and remodeling of the cytoskeleton, conducive to uptake of objects, even those that are micrometers in size. In contrast, M6PR is known to mediate uptake via the clathrin pathway, which lacks the ability to associate with the sphingomyelin/ceramide pathway. FIG. 16B shows improvement of the uptake of nanocarriers targeted to M6PR by coupling neutral sphingomyelinase to the surface of these carriers, which modulates uptake by providing this effector exogenously.

By coupling exogenous sphingomyelinase as a regulator to drug carriers as complex, uptake of those carriers by cells is enhanced. In the case of FIG. 16, enhanced uptake within cells by targeting M6PR (associated to classical endocytosis, in particular clathrin-mediated transport) is observed. Therefore, in one embodiment, the method of modulating the transcellular endothelial transmigration includes enhancement of uptake of cells generally regulated by non CAM-mediated pathways.

In another embodiment the invention relates to a method of modulating inflammation, comprising administration of a regulator of CAM-mediated endocytosis or the sphingomyelin/ceramide pathway, which is effective to regulate engulfment, uptake or transcellular transport of an agent of said inflammation.

The advantages and features of the invention are further illustrated with reference to the following examples, which are not to be construed as in any way limiting the scope of the invention but rather as illustrative of various embodiments of the invention in specific applications thereof.

Example 1

Model of Endothelial Migration

A confluent EC monolayer from human umbilical vein ECs was grown on a porous membrane through which peripheral lymphocytes isolated from healthy individuals (wild-type WBCs) can transmigrate, driven by the presence of the chemoattractant SDF1-α in the chamber underneath the ECs. Under control conditions, 77.7±2.3% wild-type WBCs underwent transmigration by 30 min, which was abrogated when K562 cells lacking the ICAM-1- and VCAM-1-binding integrins LFA-1 and VLA-4, respectively, were used (FIG. 1A). Transport of either peripheral blood lymphocytes (control) or K562 cells lacking ICAM-1- and VCAM-1-binding integrins of white blood cells (WBCs) across activated HUVEC monolayers assessed at 37° C. by counting WBCs in the bottom chamber underneath HUVEC, 30 min after adding WBCs to the upper chamber above HUVECs (black bars). Transmigration was alternatively performed prior (control) or after blocking integrins LFA-1 or VLA-4 on peripheral blood lymphocytes using monoclonal antibodies. The horizontal dashed line in FIG. 1A represents WBC transmigration at 4° C.

TEM was also inhibited by blocking LFA-1 or VLA-4 on WBCs using antibodies (40.8±11.9% or 58.8±5.6% of control, respectively; FIG. 1A) without affecting WBC capacity to transverse the porous membrane in the absence of ECs (FIG. 1B). FIG. 1B shows the results of transmigration of antibody-blocked WBCs in the presence (black bars) or absence (white bars) of HUVEC monolayer, as a control. Data are normalized to control values, and represent mean and standard errors of the mean (n≥3 experiments). *, P≤0.001 by Student's t test. These data, consistent with previous reports (Shaw S K, et al. (2001) Am J Path 01 159:2281-2291; Allingham M J, et al. (2007) J. Immunol. 179:4053-4064), validate the model.

Further, transport of activated peripheral blood lymphocytes (WBCs) across activated HUVEC monolayers was assessed at 37° C. by counting WBCs in the bottom chamber underneath HUVEC 30 min after adding WBCs to the upper chamber above HUVECs (FIG. 2A black bars). Absence of HUVEC monolayer was a control (FIG. 2A white bars). Transmigration was performed in the absence (control) or presence of filipin, methyl-β-cyclodextrin (Cdx) or amiloride. In accord with previous works (Tilghman R W, et al. (2002) FEBS Lett 525:83-87; Barreiro O, et al. (2005) Blood 105:2852-2861; Millan et al., 2006), WBC transmigration was inhibited by methyl-β-cyclodextrin (Cdx; 48.1±4.8% of control; FIG. 2A), an agent that depletes cholesterol from cells. However, filipin, a drug that binds to cholesterol and affects caveolae-mediated pathways, did not inhibit WBC transmigration (88.0±7.7% of control). Instead, amiloride, which affects $Na^+/H^+$ exchangers (Kleyman T R, et al. (1988) J Membr Biol 105:1-21) and inhibits CAM-mediated endocytosis (Muro S, et al. (2003) J Cell Sci 11 6:1599-1609), reduced WBC transmigration even to a greater extent than Cdx (38.6±3.7% of control; FIG. 2A).

Binding of activated WBCs (pre-stained with green fluorescent calcein) to activated HUVECs growing on glass coverslips was determined after co-incubation for 30 min at 37° C. in control media or media containing filipin, Cdx or amiloride, followed by fluorescence microscopy (FIG. 2B black bars). The horizontal dashed line represents binding of negative control K562 WBCs, which lack ICAM-I- and VCAM-1-binding integrins. Data are normalized to control values, and represent mean and standard errors of the mean (n≥3 experiments). *, P≤0.001 by Student's t test. Neither Cdx nor amiloride impaired the capacity of WBCs to transmigrate across the porous filter in the absence of an endothelial monolayer (FIG. 2A), or affected WBC binding to ECs (FIG. 2B).

Example 2

Model of Transcellular Vs. Paracellular Transmigration of White Blood Cells

The role of lipid domains and CAM-mediated endocytosis in paracellular versus transcellular diapedesis of leukocytes was examined. To distinguish between paracellular and transcellular TEM, WBCs were labeled with green-fluorescent calcein and diapedesis was evaluated by fluorescence and scanning electron microscopy as WBCs projecting podosomes (versus round-shaped WBCs) into or under ECs growing over glass coverslips (FIG. 3; FIG. 4).

Figure 3:
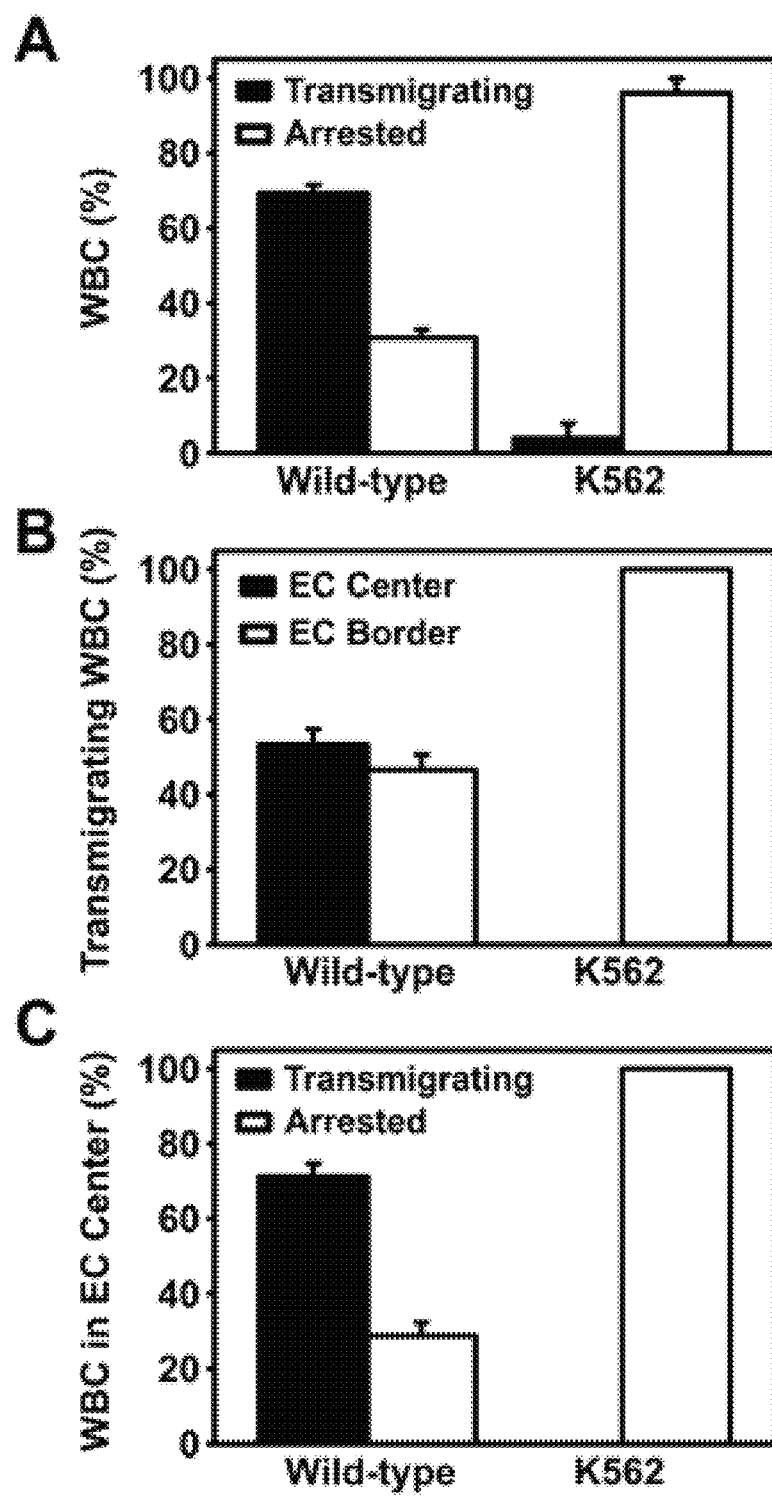
FIG. 3 provides graphs of migrating lymphocytes or K562 cells (lacking ICAM-1 and VCAM-1 binding integrins) as described in Example 2, showing (A) transmigration as measured by projecting podosomes into/under HUVECs; (B) location of transmigrated WBCs; and (C) comparison of transmigrating and arrested WBCs.

FIG. 3 shows the results of the migration of activated peripheral blood lymphocytes (control) or K562 cells lacking ICAM-1- and VCAM-1-binding integrins (pre-stained with green fluorescent calcein), determined after co-incubation for 30 min at 37° C. with activated HUVECs and analyzed by fluorescence microscopy after fixation. FIG. 3A shows WBCs projecting podosomes into/under HUVECs, scored as transmigrating (black bars) versus non-transmigrating WBCs, scored as arrested cells (round-like WBCs; white bars). FIG. 3B shows spatial distribution of transmigrating WBCs, scored as occurring at either the endothelial cell (EC) border (white bars) or center (black bars), measured at <3 μm or ≥3 μm distance from the cell border, respectively. FIG. 3C shows transmigration activity of WBCs at the EC center (black bars), scored as in FIG. 3A, compared to non-transmigrating activity (arrested; white bars) at these areas. Data are mean and standard errors of the mean (n≥30 WBCs).

FIG. 4 shows the results of the migration of activated WBCs (pre-stained with green fluorescent calcein) incubated over activated HUVECs growing on glass coverslips, determined after co-incubation for 30 min at 37° C. in control media or media containing filipin, methyl-β-cyclodextrin (Cdx) or amiloride, and analyzed by fluorescence microscopy after fixation. FIG. 4A shows WBCs projecting podosomes into/under HUVECs, scored as transmigrating (black bars). FIG. 4B shows spatial distribution of transmigrating WBCs scored as occurring at either the endothelial cell (EC) border (white bars) related to paracellular transmigration or center (black bars) related to transcellular transmigration, measured at <3 μm or ≥3 μm distance from the cell border, respectively. FIG. 4C shows transmigration activity of WBCs at the EC center (black bars), scored as in FIG. 4A, compared to non-transmigrating activity (arrested, round-like WBCs; white bars) at these areas. Data are normalized to control values (horizontal dashed lines) and represent mean and standard errors of the mean (n≥30 WBCs). *, $P \leq 0.05$; , $P \leq 0.01$; *, $P \leq 0.001$ by Student's t test.

Scanning electron micrographs showing the effect of amiloride on distribution of WBC transmigration events (FIG. 4D). White arrows indicate WBCs transmigrating at the EC border. Arrowheads mark WBCs transmigrating (white arrowheads) or arrested (black arrowheads) at EC center regions. Nu=Nucleus. Scale bar=10 μm.

In agreement with previous results and published data (Shaw et al. 2001; Yang et al. 2005; Allingham et al. 2007), 69.3±2.3% control versus 4.0±4.0% K562 WBCs transmigrated in this model (FIG. 3A; FIG. 4D). While the few transmigration events observed for K562 WBCs were associated only to the paracellular cell-cell border, control WBCs migrated similarly via the paracellular versus transcellular route (46.6±4.0% and 53.4±4.0%, respectively; FIG. 3B; FIG. 4D). All K562 WBCs located in regions away from the cell-cell border (EC center) were arrested, while 71.2±3.5% of control WBCs located in these areas underwent diapedesis (FIG. 3C and FIG. 4D).

As set forth in FIG. 2, Cdx and mainly amiloride, but not filipin, inhibited WBC TEM (80.5±6.8%, 63.8±7.3% and 108.7±8.6% of control; FIG. 4A). Cdx and amiloride shifted paracellular TEM over transcellular TEM (124.9±17.1% over 78.3±14.9% for Cdx and 139.6±34.1% over 65.5±29.7% for amiloride; FIG. 4B,D). Regarding WBCs located away from the EC borders, Cdx and amiloride decreased diapedesis (71.5±14.6% and 56.0±27.5% of control) and increased the amount of arrested WBCs (170.5±36.2% and 209.1±68.1% of control; FIGS. 4C-D).

Example 3

Study of Formation of ICAM-1-Mediated Engulfment or Docking Structures

Polymer beads coated with multiple copies of an antibody against ICAM-1 (anti-ICAM beads) were used. These have been previously used for studying aspects of leukocyte transmigration (Allingham et al., 2007; van Buul et al., 2007; van Buul et al., 2010) and CAM-mediated pathway (Muro et al., 2003; Muro et al., 2005; Muro et al., 2006; Muro et al., 2008).

Figure 5:
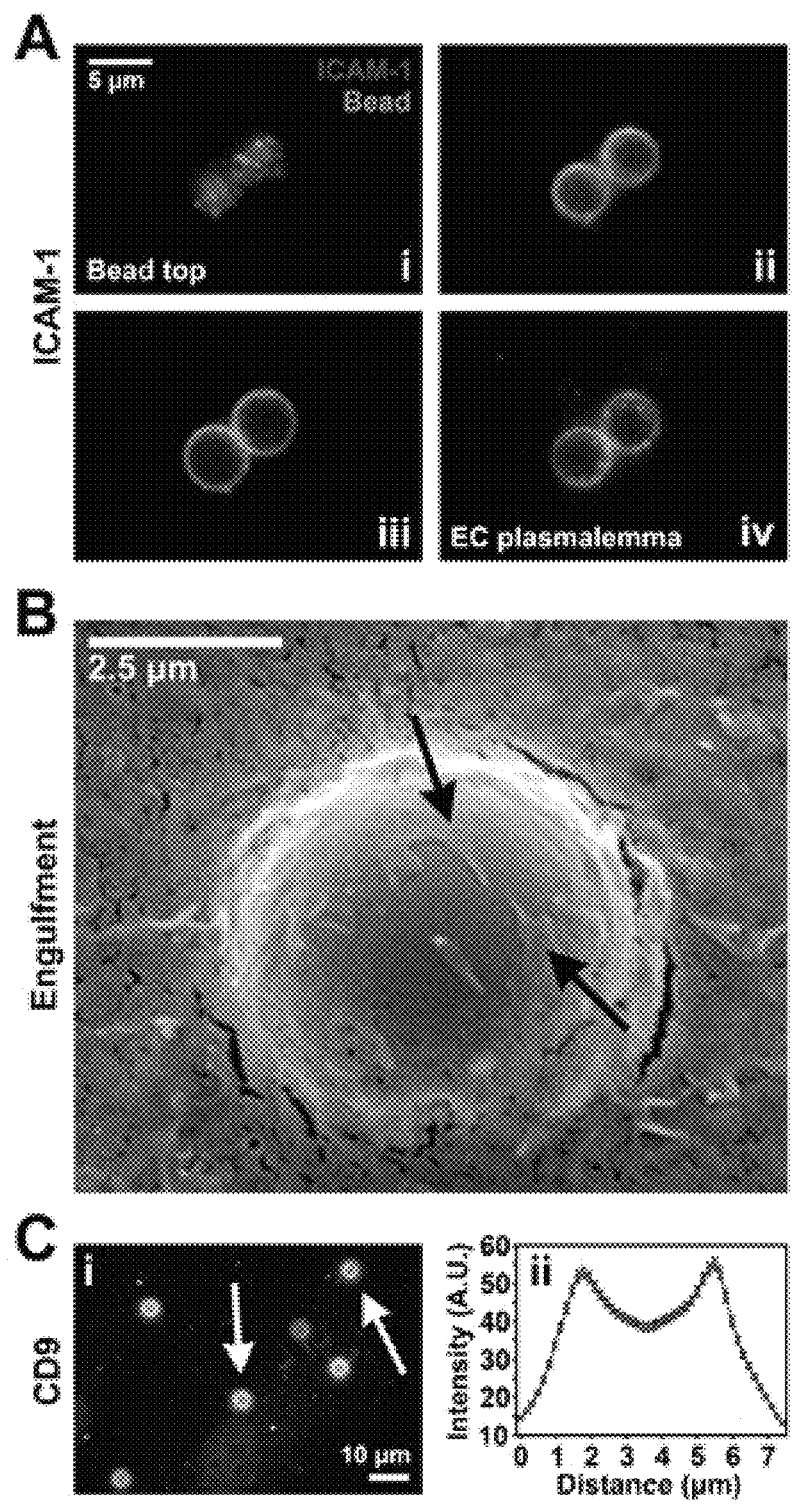
FIG. 5 provides fluorescence micrographs of anti-ICAM beads of Example 3, demonstrating (A) engulfment by ICAM-1 rich structure and (B) engulfment by the plasma membrane of the beads and (C) tetraspanin CD9 in ECs, at regions of binding of the anti-ICAM beads.

Activated HUVECs were incubated with anti-ICAM beads for 15 min at 37° C. to engage ICAM-1 on endothelial cells (ECs), followed by washing and fixation. FIG. 5A shows fluorescence micrographs obtained at different focal planes along the z-axis (i to iv, where iv is closest to the plasma membrane), after staining anti-ICAM on the surface of beads using a FITC-labeled secondary antibody and ICAM-1 on the EC surface using a Texas Red-labeled antibody. Scale bar=5 μm. The micrographs showed that, within 15 min incubation, anti-ICAM beads (immunostained in green FITC) bound to ECs and were engulfed by ICAM-1-enriched membrane protrusions (immunostained in Texas red).

FIG. 5B provides a scanning electron micrograph of an anti-ICAM bead being engulfed (arrows) by an EC. Scale bar=2.5 μm. These micrographs confirm that bead engulfment areas were morphologically similar to endothelial docking structures observed during WBC TEM (Barreiro et al., 2002; Carman and Springer 2004; Barreiro et al., 2005).

FIG. 5C provides fluorescence immunostaining of tetraspanin CD9 in ECs, at regions of binding of anti-ICAM beads. (i) Micrograph showing CD9 enrichment as ring-like structures (arrows). Scale bar=10 μm. (ii) CD9 fluorescence intensity plot at the mid cross-section plane of anti-ICAM beads. Data are mean and standard errors of the mean (n≥100 beads). These micrographs also validate the model, where analysis of the fluorescence intensity at the bead mid cross-section region showed that sites of bead engulfment by ICAM-1 engagement were enriched in tetraspanin CD9 (FIG. 5C), as reported for WBCs (Barreiro et al., 2005).

Example 4

Recruitment of Molecules to Sites of Endothelial ICAM-1 Engagement

Figure 6:
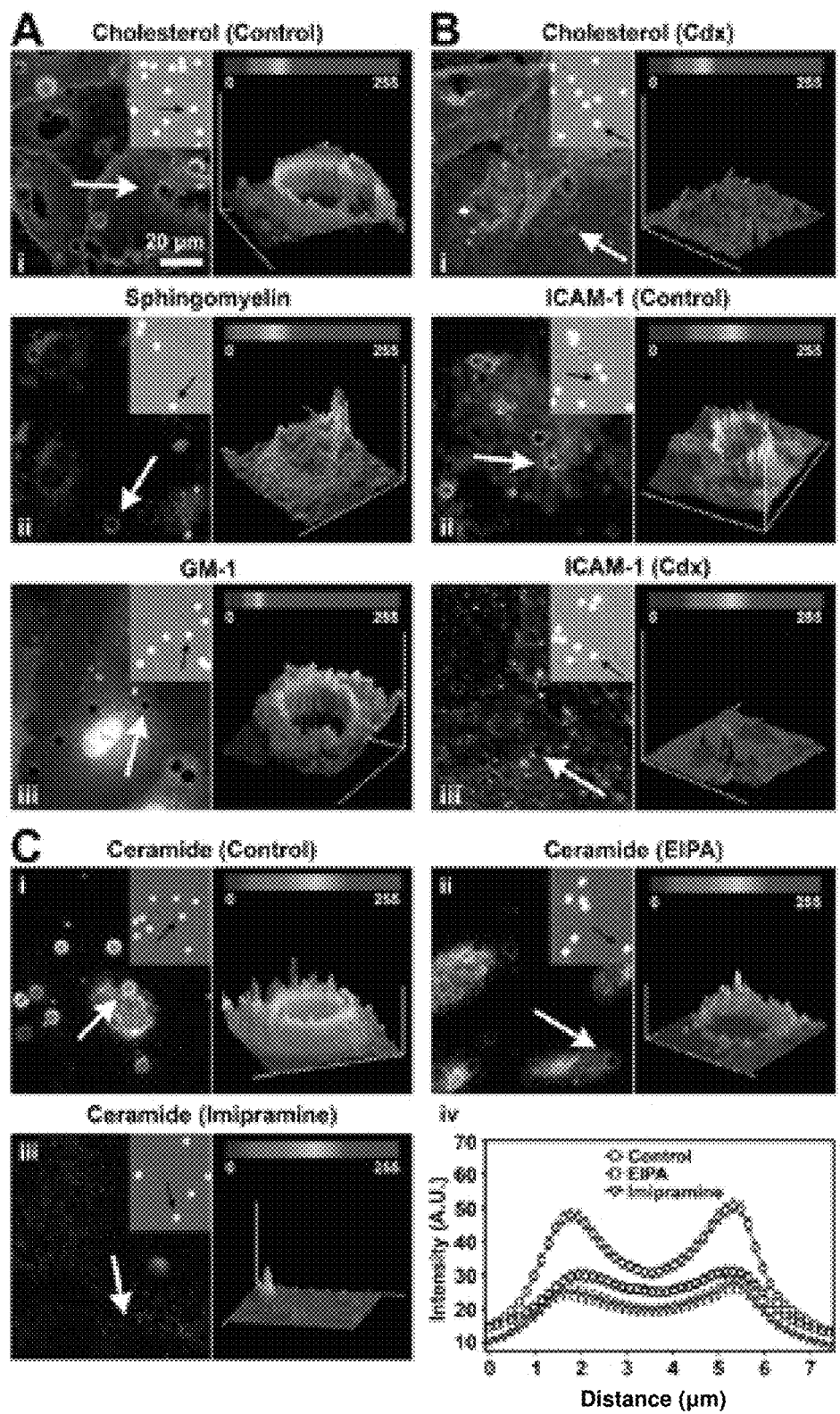
FIG. 6 provides fluorescence micrographs of Example 4, showing molecular recruitment to sites of endothelial ICAM-1 engagement of anti-ICAM beads, and modulation of this process.
Figure 7:
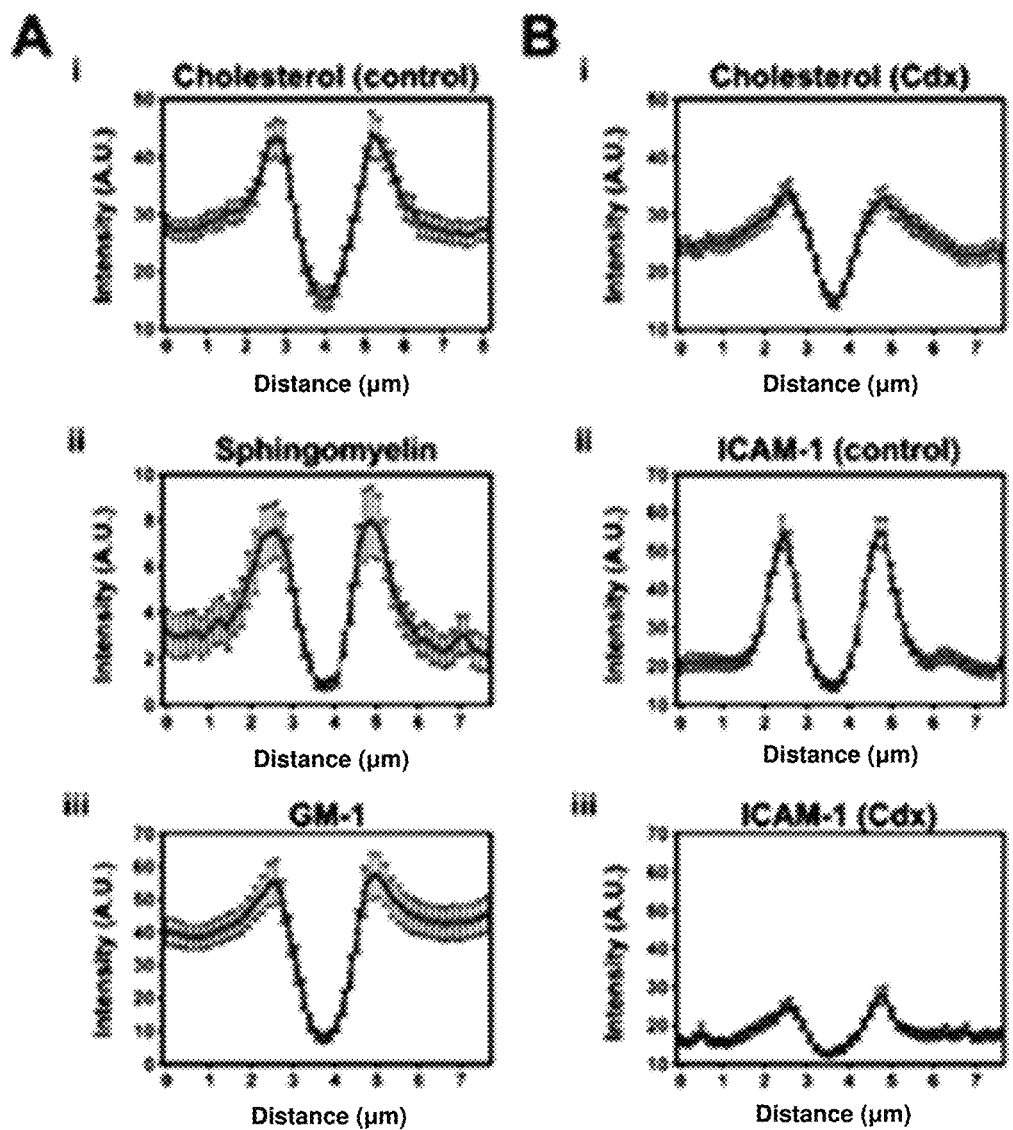
FIG. 7 provides graphs demonstrating quantification of the molecules recruited to the sites of endothelial ICAM-1 engagement of anti-ICAM beads of Example 4, and modulation of this process.

Recruitment of molecules at sites of endothelial ICAM-1 engagement by anti-ICAM beads was investigated and quantified. Activated HUVECs were incubated with anti-ICAM beads for 15 min at 37° C. to engage ICAM-1 on endothelial cells (ECs), followed by washing and fixation. FIGS. 6A and 7A show the results of cholesterol (i), sphingomyelin (ii) or ganglioside GM-1 (iii), stained using fluorescent blue filipin, green BODIPY-sphingomyelin, or Texas-red cholera toxin B, respectively. FIGS. 6B and 7B show the effect of methyl-β-cyclodextrin (Cdx) on enrichment of cholesterol labeled with blue filipin (i) or ICAM-1 immunostained with a Texas-red-labeled antibody (ii-iii) in regions of anti-ICAM-bead binding. FIG. 6C shows immunostaining of ceramide using a Texas-red labeled antibody in regions of anti-ICAM-bead binding in control (i), EIPA-treated (ii), and imipramine-treated (iii) cells. Left panels show fluorescence micrographs and phase-contrast insets of bound beads. Right panels show pseudocolored fluorescence intensity reconstructions of molecules in the EC plasmalemma at areas of bound beads, which are indicated by arrows on their respective left panels and insets. Scale bar=20 µm. (iv) Ceramide fluorescence intensity plots at the mid cross-section plane of anti-ICAM beads bound to ECs under control (circles), imipramine (triangles), or EIPA (squares) conditions. Data are mean and standard errors of the mean (n≥150 beads) in FIG. 6. Data represent mean and standard errors of the mean (n≥65 beads) in FIG. 7.

Fluorescence intensity of cholesterol, sphingomyelin and ganglioside GM1 was increased by 1.6±0.04-fold, 3.1±0.1-fold, and 1.4±0.1-fold, respectively, in regions of bead engulfment by ICAM-1 engagement over adjacent areas (FIG. 7A). Cdx treatment to chelate cholesterol (confirmed in FIG. 6Bi and FIG. 7Bi) decreased ICAM-1 enrichment in areas of bead engulfment (43% decrease; FIG. 6Bii-iii; FIG. 7Bii-iii).

Figure 8:
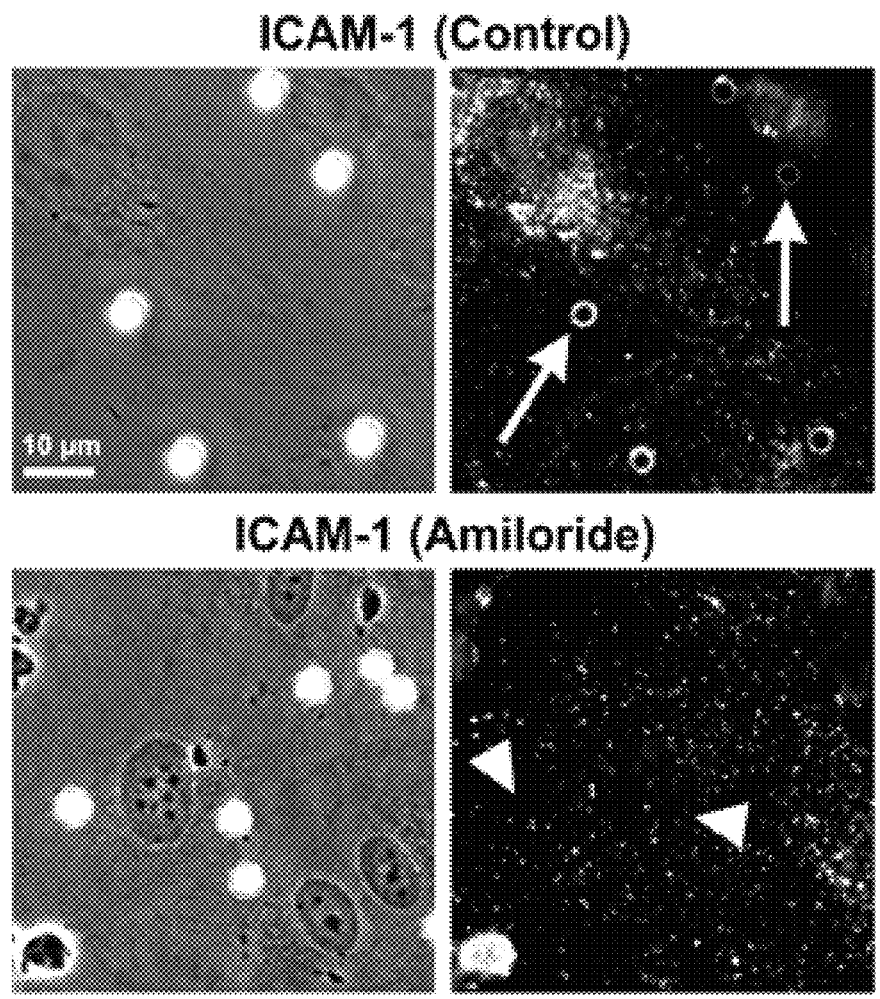
FIG. 8 provides fluorescence micrographs showing the effects of amiloride on the formation of ICAM-1-rich endothelial docking-like structures by anti-ICAM beads, as described in Example 4.

Similarly, treatment with amiloride to inhibit CAM-mediated pathway decreased ICAM-1 enrichment in engulfment protrusions (22.9% decrease). Fluorescence micrographs of FIG. 8 show activated HUVECs incubated for 15 min at 37° C. with anti-ICAM beads to engage ICAM-1 on endothelial cells (ECs), under control conditions (top panel) or in the presence of amiloride (bottom panel). Cells were washed and fixed, ICAM-1 was immunostained using a Texas-red-labeled antibody, and samples were analyzed by fluorescence microscopy (right panels) and phase contrast (left panels). Presence or absence of bead engulfment is marked with arrows or arrowheads, respectively. Scale bar=10 pm.

Additionally, ceramide was tested for at regions of ICAM-1 engagement by anti-ICAM beads.

Example 5

Study of ASM Association with the CAM-Mediated Pathway

As shown in FIG. 6 of Example 4 above, imipramine, a drug that inhibits acid sphingomyelinase (ASM), impaired ceramide enrichment in areas of bead engulfment associated to ICAM-1 engagement (23.6% decrease; FIG. 6Ciii-iv), implicating for the first time ASM in ICAM-1-driven formation of endothelial docking-like structures.

Figure 9:
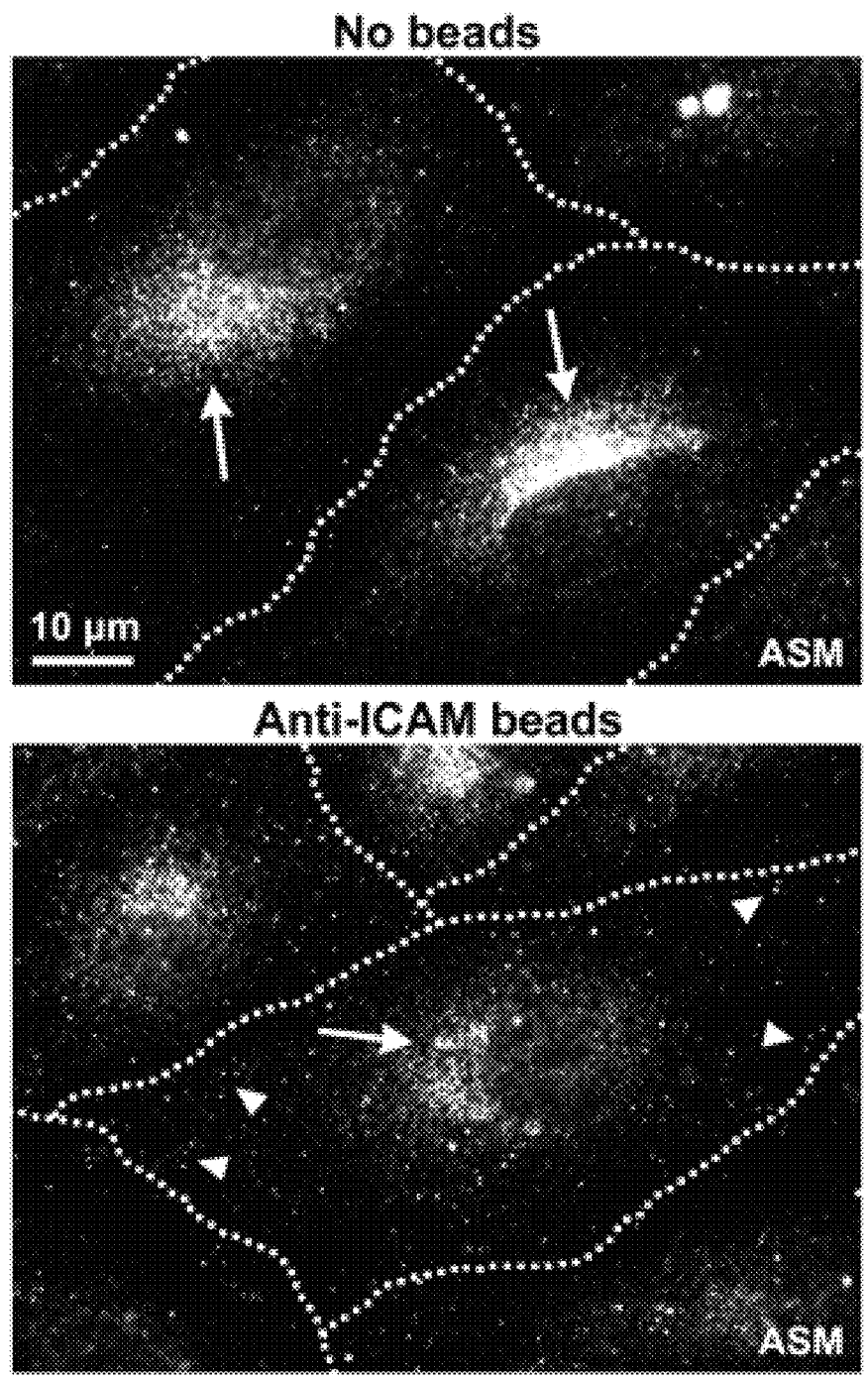
FIG. 9 provides fluorescence micrographs showing distribution of endothelial ASM upon ICAM-1 engagement by anti-ICAM beads, as described in Example 5.

Immunofluorescence of ASM in ECs showed that, in absence of ICAM-1 engagement by anti-ICAM beads, most ASM located to vesicular compartments (likely lysosomes) in the perinuclear region of cells (41.8±4.7 vesicles/cell), while only a few ASM-positive vesicles were found outside the perinuclear area (23.7 k3.3 vesicles/cell; FIG. 9). Activated HUVECs were incubated in the absence (FIG. 9; top panel) or presence (FIG. 9; bottom panel) of anti-ICAM beads for 30 minutes at 37° C. Cells were fixed and permeabilized, and ASM was immunostained in Texas-red. Arrowheads mark ASM at the perinuclear region of cells. Arrows mark ASM at the cell periphery. Dashed lines mark the cell borders, as observed by phase contrast. Scale bar=10 µm.

Activated HUVECs were incubated with anti-ICAM, anti-VCAM or anti-M6PR beads for 15 minutes at 37° C. to engage these molecules on endothelial cells (ECs), followed by washing and fixation. Fluorescence immunostaining of ASM (FIG. 10A; bottom panels) in regions of respective bead binding (FIG. 10A; phase-contrast, top panels). FIG. 10B provides fluorescence microscopy showing immunostaining of ASM (green), and ICAM-1 (red, i-iv) or NHE1 (red, v-viii). Boxes indicate the respective beads and bead regions selected for enlargement in iii and vii, and in iv and viii. Scale bars=10 µm, 2 µm, or 0.5 µm, as indicated. ICAM-1 engagement by anti-ICAM beads lead to appearance of ASM-positive vesicles at the cell periphery (1.7-fold and 2.3-fold increase at 15 min and 30 min), and bead engulfment areas became enriched in ASM (FIG. 10A). As negative controls for ICAM-1 specificity, beads coated with antibodies to VCAM-1, also involved in WBC TEM, or mannose-6-phosphate receptor (MGPR), involved in clathrin-mediated transport of ASM (Willingham M C, et al. (1981) PNAS USA 78:6967-6971), did not elicit ASM recruitment (FIG. 10A).

Figure 11:
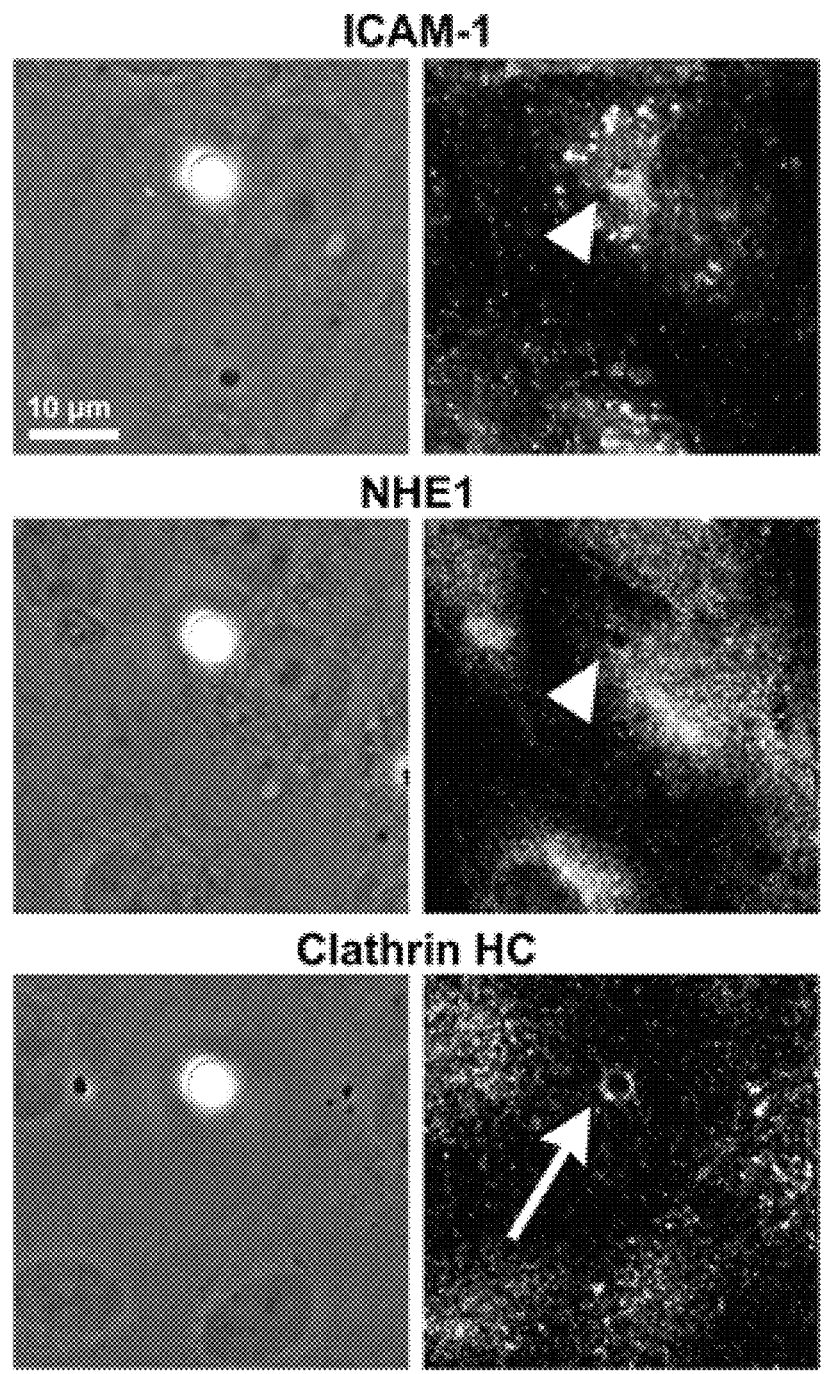
FIG. 11 provides fluorescence micrographs showing recruitment of molecules at sites of endothelial engagement of a classical clathrin-associated receptor mannose-6-phosphate receptor (M6PR) by anti-M6PR beads.

Activated HUVECs were incubated with anti-mannose-6-phosphate receptor (M6PR) beads for 15 min at 37° C. to engage M6PR on endothelial cells (ECs), followed by washing and fixation. Phase contrast (FIG. 11; left panels) and fluorescence micrographs (FIG. 11; right panels) were obtained at the mid cross-section plane of beads after immunostaining ICAM-1 (top), NHE1 (middle), or clathrin heavy chain (bottom) in Texas Red. Arrowheads indicate lack of enrichment of the corresponding marker around beads. Arrows indicate enrichment of the corresponding marker around beads. Scale bar=10 µm. Anti-M6PR beads induced recruitment neither of ICAM-1 nor NHE1, but recruited clathrin heavy chain (FIG. 11), validating the specificity of this model.

In addition, areas of bead engulfment mediated by ICAM-1 engagement (FIG. 10B) revealed that ASM co-localized well with ICAM-1 and NHE1 (85.1±2.9% and 85.3±3.4% co-localization). At high magnification, ASM appeared to distribute within ICAM-1- and NHE1-lined vesicular structures (FIG. 10 Biv,viii), supporting secretion of ASM associated to CAM-mediated pathway.

Example 6

Role of ASM on CAM-Endocytosis and Related Events

As shown in Table 1, inhibition of ASM with imipramine or NHE1 with amiloride, and $Na^+$ depletion to impair $Na^+/H^+$ transport and acidification (but not filipin, which affects caveolae) decreased endocytosis of anti-ICAM beads by ECs in culture (from ~7% to ~60% of control). This was verified using genetically modified models to circumvent specificity concerns of pharmacological inhibitors. Using ECs isolated from wild-type versus $ASM^{-/-}$ mice, it was observed that lack of ASM reduced endocytosis of anti-ICAM beads (25% of ECs isolated from wild-type mice; Table 1).

TABLE 1

| | Internalization (%) |
|---|---|
| HUVECs | |
| Control | 100.0 ± 7.6 |
| Amiloride | 13.8 ± 3.3** |
| Imipramine | 61.9 ± 6.7** |
| $Na^+$ depletion | 7.4 ± 2.5** |
| Filipin | 107.2 ± 1.5 |

TABLE 1-continued

| | Internalization (%) |
|---|---|
| MLECs | |
| Control | 100.0 ± 25.4 |
| ASM$^{-/-}$ | 25.4 ± 10.5* |

Values are normalized to controls
* and ** indicate p ≤ 0.05 and p ≤ 0.001, respectively.
n ≥ 10 micrographs from 2 replicates.

Figure 12:
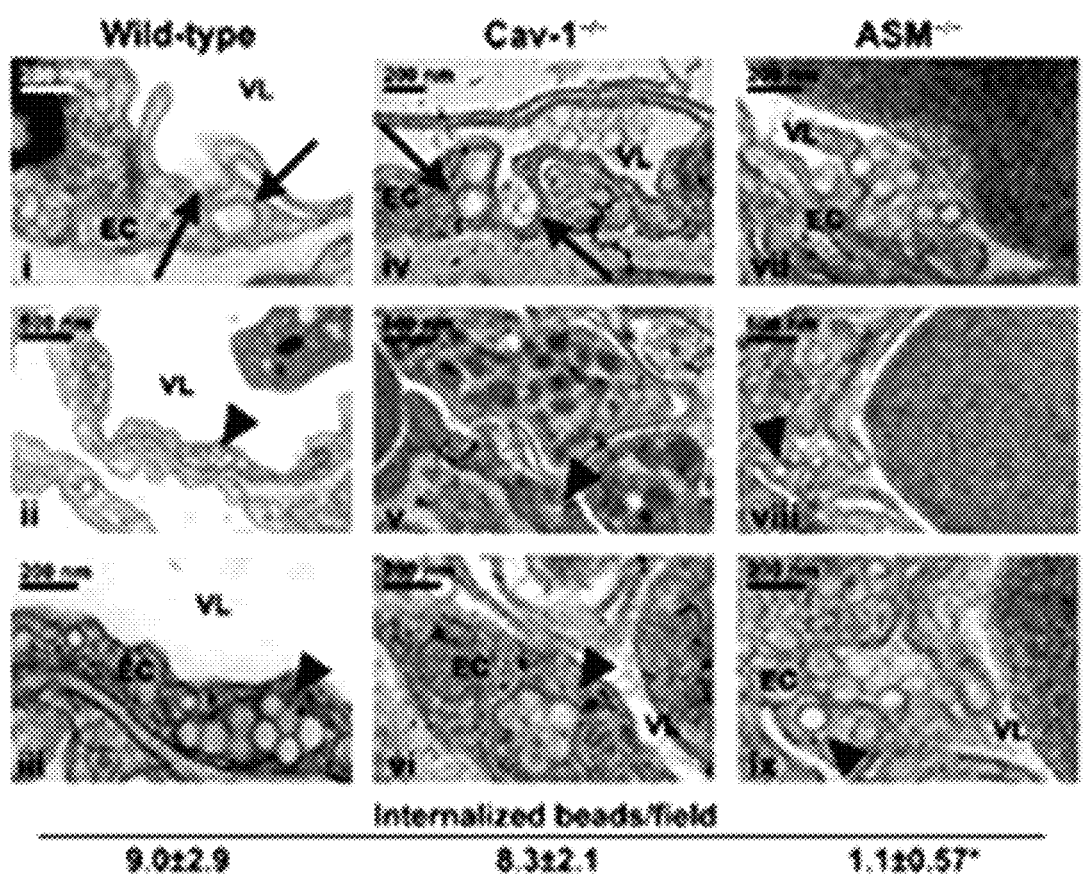
FIG. 12 provides electron microscopy images from the in vivo testing of Example 6, demonstrating presence or absence of CAM-mediated endocytosis in wild type (i-iii) caveolin-1$^{-/-}$ (iv-vi) and ASM$^{-/-}$ (vii-ix) mice.

This was further confirmed in vivo by injecting anti-ICAM beads into wild-type (FIG. 12 i-iii), caveolin-1$^{-/-}$ (FIG. 12iv-vi), or ASM$^{-/-}$ (FIG. 12 vii-ix) mice intravenously under anesthesia, and after 3 h lungs were isolated, perfused, and processed for transmission electron microscopy. Arrows in FIG. 12 indicate beads being internalized in endothelial invaginations. Arrowheads indicate beads fully internalized in intracellular vesicles. EC=endothelial cell, VL=(blood) vessel lumen. Scale bars=200 nm or 500 nm, as indicated. The number of beads internalized within ECs was quantified from the micrographs. Data are mean and standard errors of the mean (n≥13 micrographs). *, P≤0.05 by Student's t test. As in cell cultures, engulfment leading to endocytosis of anti-ICAM beads by ECs was inhibited in ASM$^{-/-}$ mice but not in caveolin-1$^{-/-}$ mice (12.2% and 92.8% of wild-type mice).

Additionally, in ASM$^{-/-}$ mice, fewer membrane invaginations were detected in association with anti-ICAM beads (FIG. 12i,iv,vii), and the beads internalized in these mice were individually located within vesicles (FIG. 12ix), in contrast to large vesicular structures containing multiple beads observed in wild-type and caveolin-1$^{-/-}$ mice (FIG. 12iii,vi).

Figure 13:
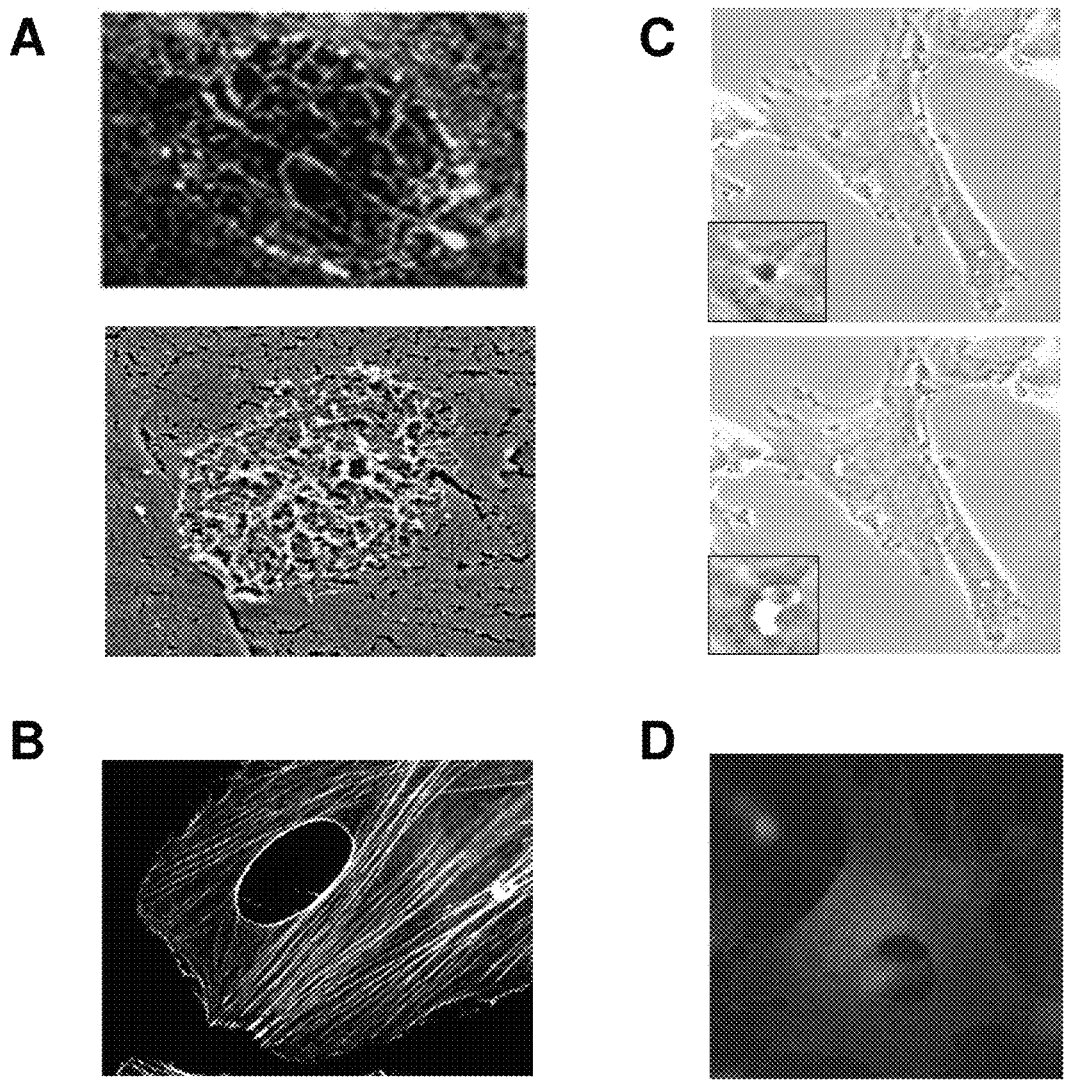
FIG. 13 provides images of the experiments performed in Example 6; (A) fluorescence micrographs showing formation of ICAM-1-rich vesicles coalescing into a pore; (B) fluorescence microscopy images showing said pore surrounded by actin filaments; (C) images showing formation of pores in the EC underneath a bound particle; and (D) formation of transmigration pores in binding of WBCs to HUVECs.

Validating this observation on the role of CAM- and sphingomyelin/ceramide pathways on formation of transmigratory pores, it was further observed that engagement of ICAM-1 in control ECs using anti-ICAM particles, carriers and protein conjugates lead to formation of multiple vesicles at the plasma membrane, which coalesced into large pore-like structures supported by or in association with the actin cytoskeleton (FIG. 13A-C). This is similar to pores that open across ECs during transmigration of WBCs (FIG. 13D). Activated HUVECs were incubated with anti-ICAM conjugates for 15 min at 37° C. to allow engagement of ICAM-1 in the cell surface, followed by washing cells and fixation. ICAM-1 in the surface of the plasma membrane was then stained using anti-ICAM and a secondary antibody labeled in Texas red (yellowish in the picture). Cells were then washed and permeabilized to access internal compartments. ICAM-1 in internal structures was then stained with anti-ICAM followed by a secondary antibody labeled in green FITC. Imaging by fluorescence microscopy permitted to observe multiple small vesicles enriched in ICAM-1 just underneath the cell surface. These vesicles appeared to clealesce or merge in large structures preliminary to pore formation. A similar experiment with similar result is shown by scanning electron microscopy in FIG. 13B. Activated HUVECs were incubated with 4.5 pm diameter anti-ICAM particles and imaged by dynamic phase-contrast microscopy. A pore forms in the EC underneath a bound particle, as shown in FIG. 13C.

Example 7

Study of Acid Sphingomyelinase Association in Leukocyte Transcellular Transmigration Migration of activated WBCs (pre-stained with green fluorescent calcein) incubated over activated HUVECs growing on glass coverslips, determined after co-incubation for 30 min at 37° C. in control media or media containing imipramine, and analyzed by fluorescence microscopy after fixation.

Figure 10:
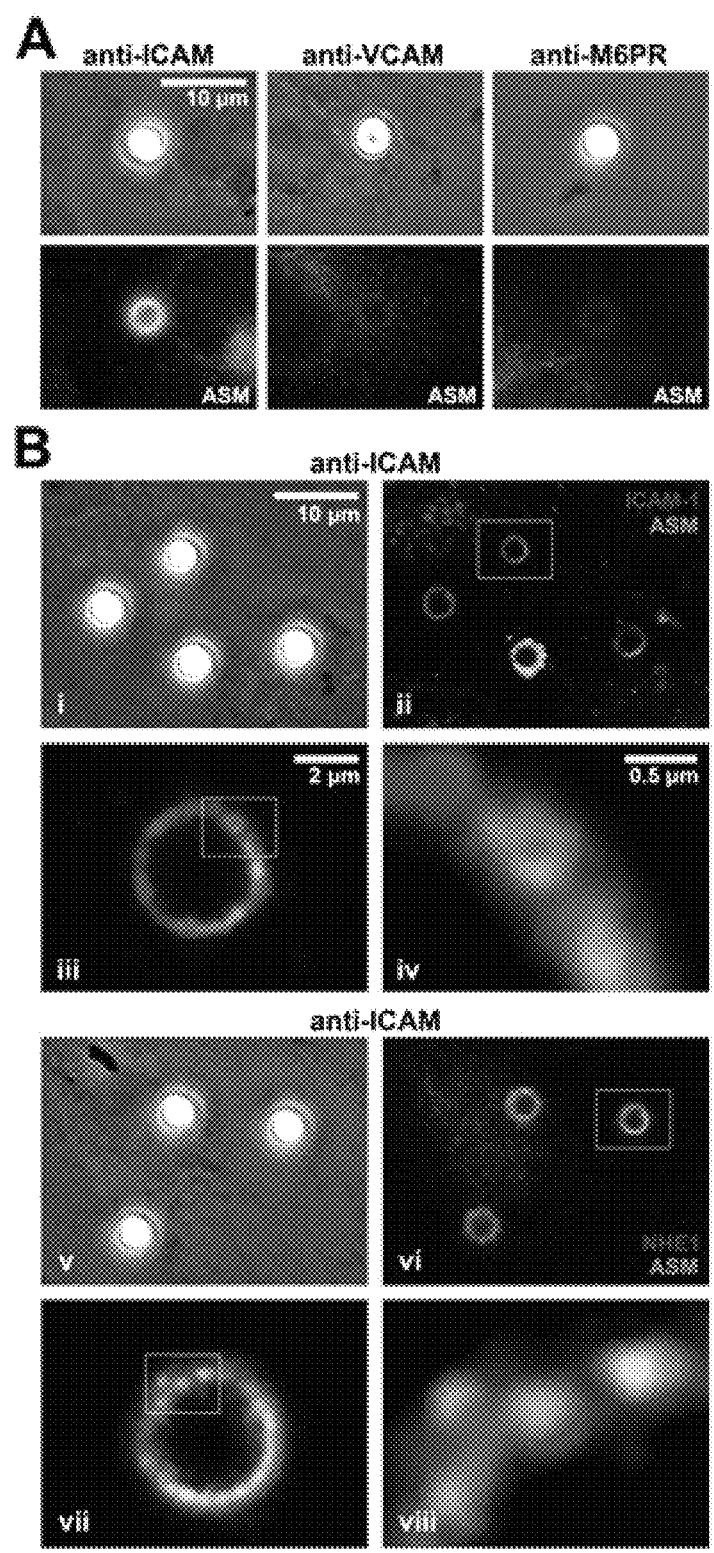
FIG. 10 provides fluorescence micrographs showing redistribution of endothelial ASM and NHE1 upon ICAM-1 engagement, as described in Example 5.
Figure 14:
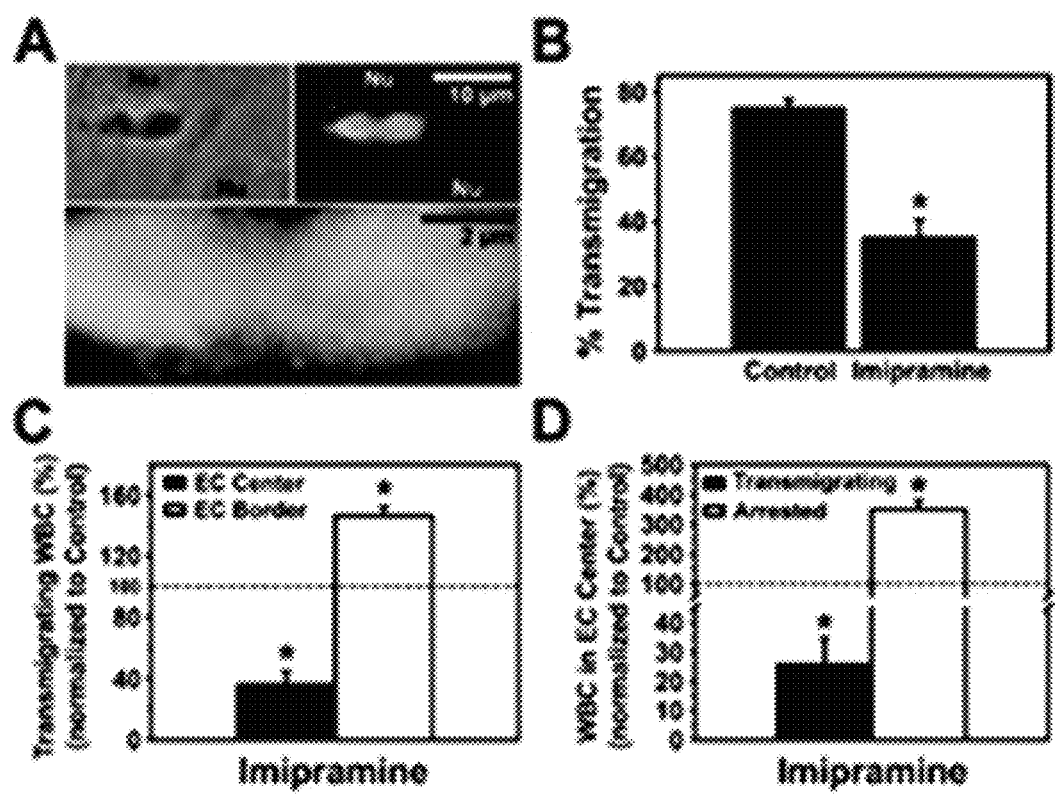
FIG. 14 provides the results of the experiments performed in Example 7 (A) images showing immunostaining of ASM at the WBC-HUVEC interface; (B) graph of transmigration as measured by projecting podosomes into/under HUVECs; (C) graph of determined location of transmigrated WBCs; and (D) comparison of transmigrating and arrested WBCs.

Fluorescence microscopy revealed enrichment of ASM (immunostained in Texas red) in the interface between ECs and transmigrating peripheral lymphocytes (stained with green calcein; FIG. 14A). FIG. 14A shows phase contrast (left panel) and Texas-red immunostaining of ASM (right and bottom panels) at the WBC-HUVEC interface in control conditions. Nu=nucleus. Scale bars=10 µm or 2 µm, as indicated. This is similar to endothelial docking-like structures formed upon sole engagement of ICAM-1 by anti-ICAM beads, as shown in FIG. 10.

Furthermore, imipramine treatment to inhibit ASM led to a decrease in WBC transmigration (46.6±7.6% of control; FIG. 14B), without affecting WBC binding to ECs (108.0±18.6% of control). In FIG. 14B WBCs projecting podosomes into/under HUVECs, scored as transmigrating (white bars).

As shown for Cdx and amiloride in FIG. 4, ASM inhibition with imipramine decreased the level of transcellular TEM, while paracellular TEM increased (FIG. 14C). In FIG. 14C, spatial distribution of transmigrating WBCs was scored as occurring at either the endothelial cell (EC) border (white bars) or center (black bars), measured at <3 µm or ≥3 µm distance from the cell border, respectively.

From the WBC population located away from paracellular areas, there was a decrease in transmigrating WBCs and an increase in arrested WBCs (FIG. 14D), suggesting that ASM activity that linked to ICAM-1-engagement and NHE1-dependent CAM-mediated pathway is involved in transcellular TEM of WBCs. In FIG. 14D, transmigration activity of WBCs at the EC center (black bars) was scored as in (B), compared to non-transmigrating activity (arrested, round-like WBCs; white bars) at these areas. Data are normalized to control values (horizontal dashed lines), and represent mean and standard errors of the mean (n≥100 WBCs). * P≤0.01 by Student's t test.

Example 8

Enhanced Transport of Carriers by Cells Via Coupling to Sphingomyelinases

Figure 15:
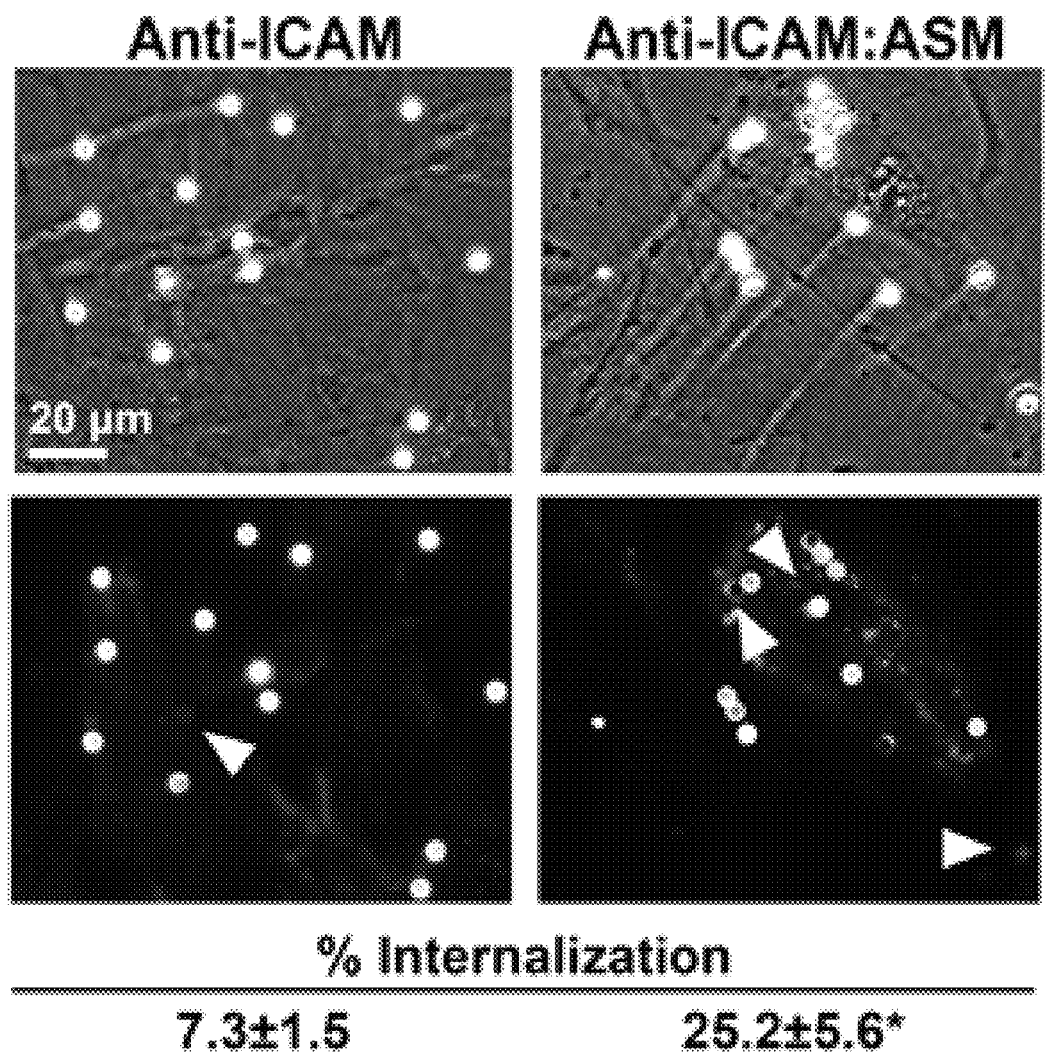
FIG. 15 provides fluorescence micrographs visualizing the effect of coupling acid sphingomyelinase to ICAM-1-targeted particles as described in Example 8, showing (A) total amount of particles and (B) surface located particles, which enhances uptake of particles by cells deficient in this enzyme.

As shown in FIG. 15, polystyrene particles (4.5 µm diameter), a model for a carrier of diagnostic and/or therapeutic agents, were coated with anti-ICAM to target ECs and ASM, to recover uptake and intracellular transport of carriers by facilitating endocytosis in ASM$^{-/-}$ ECs, which are otherwise voided of ASM and hence do not support CAM-mediated pathway (as shown in Table 1). Particles only coated with anti-ICAM but not ASM were used as negative controls for lack of internalization. The cells were incubated with the particles for 30 min at 37° C. to first allow binding of particles to ICAM-1 on the cell surface. Then, non-bound particles were washed off and cells were incubated in control media for 1 h at 37° C. to permit potential endocytosis of bound particles. Cells were finally washed and fixed. Surface-bound non-internalized particles were immunostained using a secondary antibody labeled with Texas red. This antibody can only bind to anti-ICAM on surface-located beads, while it can not access particles internalized within the cells.

Samples were analyzed by fluorescence microscopy to visualize total beads associated to cells by phase contrast (upper panels) and fluorescence microscopy to visualize non-internalized particles (lower panels, arrowheads), from which the percent of internalization of particles was calculated. Data represent mean and standard errors of the mean (n≥15 ECs). * P≤0.05 by Student's t test. Scale bar=20 μm.

As shown in FIG. 16A, polystyrene particles (1 μm diameter), a model for a carrier of diagnostic and/or therapeutic agents, were coated with anti-ICAM or anti-M6PR, a cell surface marker related to classical endocytic transport pathway (clathrin-mediated uptake or transcytosis, in particular). Particles targeted to M6PR were not efficient in being transported by cells, in contrast to particles targeted to ICAM-1, when tested either at 30 min or 3 h incubation at 37° C. FIG. 16B shows that incorporation of a sphingomyelinase (neutral sphigomyelinase, in particular) but not a control protein (IgG) to anti-M6PR particles enhanced transport by cells by providing this element of the CAM- and sphingomyelin/ceramide pathway. Data represent mean and standard errors of the mean (n≥15 ECs). * P≤0.05 by Student's t test.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of potentiating engulfment, uptake or transcellular migration of an agent,
   wherein the agent is complexed to a carrier targeted to a non-ICAM cell surface molecule or receptor,
the method comprising administering a regulator of CAM-mediated endocytosis or the sphingomyelin/ceramide pathway, said regulator exogenously modulating the non-ICAM cell surface molecule or receptor,
   wherein such administration is effective to enhance cellular uptake of the agent and/or transcellular transport of the agent via the non-ICAM cell surface molecule or receptor,
   wherein the regulator is neutral sphingomyelinase; and
   wherein the carrier is targeted to M6PR.
2. The method of claim 1, wherein the agent comprises a drug.
3. The method of claim 1, wherein the agent is selected from the group consisting of autologous white blood cells, foreign white blood cells, pathogens, drugs, research probes, analytical probes, molecular probes, diagnostic agents, therapeutic agents, biologically active agents, research agents, analytical agents, imaging agents, monitoring agents, enzymes, proteins, peptides, hormones, lipids, sugars, nucleic acids, lipoproteins, and chemicals.
4. The method of claim 1, wherein the agent is autologous white blood cells or foreign white blood cells.
5. The method of claim 1, wherein the agent is a pathogen.
6. The method of claim 1, wherein the agent is a diagnostic agent.
7. The method of claim 1, wherein the agent is a therapeutic agent.
8. The method of claim 1, wherein the agent is an imaging agent.
9. The method of claim 1, wherein the carrier s a polymer.
10. The method of claim 1, wherein the administration of the regulator is in vitro.
11. The method of claim 1, wherein the administration of the regulator is in vivo to a patient in need of such administration.
12. The method of claim 11, wherein the administration of the regulator provides effective levels of the regulator to the endothelium of the patient.
13. The method of claim 11, wherein the administration is parenteral administration, intraperitoneal administration, intravenous administration, intramuscular administration or subcutaneous administration.
14. The method of claim 1, wherein the non-ICAM cell surface molecule or receptor mediates uptake via a clathrin-mediated pathway.

* * * * *

UNITED STATES PATENT AND TRADEMARK OFFICE
CERTIFICATE OF CORRECTION

PATENT NO. : 9,901,625 B2
APPLICATION NO. : 13/652165
DATED : February 27, 2018
INVENTOR(S) : Silvia Muro Galindo Page 1 of 1

It is certified that error appears in the above-identified patent and that said Letters Patent is hereby corrected as shown below:

Column 1, Line 65: "132" should be -- β2 --.

Column 24, Line 25: "s" should be -- is --.

Signed and Sealed this
Fifteenth Day of May, 2018

Andrei Iancu
*Director of the United States Patent and Trademark Office*